United States Patent [19]
Andrews et al.

[11] Patent Number: 6,090,825
[45] Date of Patent: Jul. 18, 2000

[54] OXAZOLE DERIVATIVES AS ANTAGONISTS OF ALPHA 1C ANDRENERGIC RECEPTORS

[75] Inventors: Robert Carl Andrews, Durham; Peter Jonathan Brown, Chapel Hill; Rodolfo Cadilla, Durham; David Harold Drewry, Durham; Michael Joseph Luzzio, Durham; Brian Edward Marron, Durham, all of N.C.; Stewart Alwyn Noble, Upper Saddle, N.J.

[73] Assignee: Glaxo Wellcome Inc., Research Triangle Park, N.C.

[21] Appl. No.: 08/849,016

[22] PCT Filed: Nov. 20, 1995

[86] PCT No.: PCT/EP95/04552

§ 371 Date: Jun. 3, 1997

§ 102(e) Date: Jun. 3, 1997

[87] PCT Pub. No.: WO96/16049

PCT Pub. Date: May 30, 1996

[30] Foreign Application Priority Data

Nov. 23, 1994 [GB] United Kingdom ............... 9423638
Mar. 28, 1995 [GB] United Kingdom ............... 9506282
Sep. 29, 1995 [GB] United Kingdom ............... 9519885

[51] Int. Cl.[7] ............... A61K 31/445; C07D 413/02; A61P 9/06; A61P 17/14
[52] U.S. Cl. ............................. 514/326; 546/209
[58] Field of Search .............. 546/209; 514/326

[56] References Cited

U.S. PATENT DOCUMENTS 3,966,748 6/1976 Hofmann et al. ............... 546/209
5,324,723 6/1994 Baker et al. ............... 546/209

FOREIGN PATENT DOCUMENTS 0 582 164 2/1994 European Pat. Off. .
2 081 532 12/1971 France .
2 340 944 9/1977 France .

OTHER PUBLICATIONS

Chemical Abstracts, vol. 91, No. 5, Jul. 30 1979, Columbus, OH, US, Abstract No. 39463g, p. 634.

*Primary Examiner*—Mukund J. Shah
*Assistant Examiner*—Brenda Coleman
*Attorney, Agent, or Firm*—Robert H. Brink

[57] ABSTRACT

Oxazole compounds having formula (I) wherein $R^1$ and $R^3$ are selected from the group consisting of hydrogen, hydroxy, $C_{1-6}$alkyl, $C_{1-6}$alkoxy, $C_{1-6}$alkoxyC$_{1-6}$alkyl, phenyl or phenyl mono- or disubstituted with $C_{1-6}$alkyl, halogen, hydroxy, $C_{1-6}$alkoxy, aminosulfonyl, hydroxyC$_{1-6}$alkyl, $C_{1-6}$alkylsulfonylaminoC$_{1-6}$alkyl or carbamylC$_{1-6}$alkylaminosulfonyl; $R^2$ is selected from hydrogen, $C_{1-6}$alkyl, hydroxyC$_{1-6}$alkyl, $C_{1-6}$alkoxy, $C_{1-6}$alkoxyC$_{1-6}$alkyl or (fluorinated $C_{1-6}$alkyl)oxyC$_{1-6}$alkyl; W is a $C_{1-6}$alkylene chain or nitrogen; m is independently the integer 0 or 1; X is CH or nitrogen, provided that when W is nitrogen then X is CH; q is independently an integer selected from the group consisting of 1, 2, 3 or 4; or a pharmaceutically acceptable acid-addition or base-addition salt thereof, pharmaceutical compositions containing them and their use in therapy.

(I)

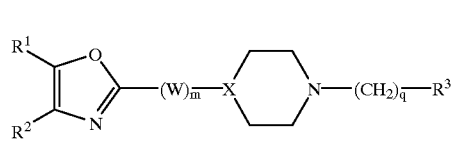

14 Claims, No Drawings

OXAZOLE DERIVATIVES AS ANTAGONISTS OF ALPHA 1C ANDRENERGIC RECEPTORS

This application is filed pursuant to 35 U.S.C. § 371 as a United States National Phase Application of International Application No. PCT/EP95/04552 filed Nov. 20, 1995 which claims priority from GB9423638.7 filed Nov. 23, 1994; GB9506282.4 filed Mar. 28, 1995; and GB9519885.9 filed Sep. 29, 1995.

FIELD OF THE INVENTION

The present invention is directed to pharmaceutically active organic compounds containing two heterocylic ring structures.

BACKGROUND OF THE INVENTION

Benign prostatic hyperplasia (BPH) is a benign neoplasm found primarily in older males, see H. Lepor, *Urologic Clinics of North America*, 17, No. 3, 651–659 (1990). BPH clinical manifestations include bladder outlet obstruction resulting from enlargement of the prostate gland. The condition is most often treated by transurethral prostatectomy, see H. Lepor, et al. *The Journal of Urology*, 148, 1467–1474 (1992).

The prostate has been demonstrated to be rich in alpha 1 ( -1) adrenergic receptors, see s. Raz, et al, *British Journal of Urology*, 45, 663–667 (1973). It has been reported that BPH can be treated with an -1 adrenergic receptor blocker, which may act by relaxing the tension of prostate smooth muscle, thus relieving the symptoms of infravesical obstruction, see H. Lepor et al, supra at 1473 and Forray et al., *Molecular Pharmacology*, 45, 703–708 (1994). Recently the -1 adrenergic receptor mRNA from human prostate has been analyzed and three subtypes have been identified: -1B, -1C and -1D, with -1C comprising 70% of the mRNA. In August of 1994 the nomenclature of the -1B, -1C and -1D subtypes of the alpha adrenergic receptors were renamed as -1B, -1A and -1D respectively, see *J. Med. Chem.*, vol. 38 No. 10, 1579–1581 (1995) and Ford et al. *Trends Pharmacol. Sci.*, 1994, 15, 167–170. In the present invention, the old nomenclature -1C is used to define that subtype adrenergic receptor that is currently referred to as -1A under the aforementioned August 1994 nomenclature.

Different adrenergic receptors may account for the cardiovascular and central nervous system side effects caused by nondiscriminator blockage of -1 adrenergic receptor subtypes, see D. T. Price, et al, *The Journal of Urology*, 150, 546–551 (1993) and PCT Application WO 94/10989. -1 adrenergic antagonists which bind selectively to the -1C adrenergic receptor subtype preferentially over the -1B and -1D subtypes have been claimed as useful in the treatment of BPH, see PCT Application WO 94/10989, supra. Testosterone 5 -reductase inhibitors such as Proscar™ (Merck) have been shown to be useful in the treatment of a variety of androgen responsive diseases such as BPH and prostate cancer, see Frye, et al, U.S. Pat. No. 5,302,589, PCT Application WO 94/10989, supra. Additionally, -1 adrenergic receptor antagonists and dopamine $D_2$ antagonists in combination have been shown to be useful as an antipsychotic treatment, see Hrib, et al, *J. Med. Chem.*, 37, 2308–2314 (1994). -1-adrenergic antagonists have also been shown to differentially control serotonin release in the hippocampus and striatum, see Rouquier, et al, *Eur. J. Pharmacol.*, 261(1–2), 59–64 (1994), have an effect on susceptibility to malignant arrhythmias, see Billman, *J. Cardiovasc. Pharmacol.*, 24(3), 394–402 (1994), to possess dopamine receptor agonist activity and 5-HT receptor antagonist activity, see PCT patent application WO 9305035, to effect hyperthermia and hyperglycemia, see Nonogaki K., et al, *Eur. J. Pharmacol.*,262(1–2):177–180 (1994), to have a role in treatment of obstructive detrusor instability, see C. R. Chapple, et al, *Brit. J. of Urology*, 73, 117–123 (1994), and to have hemodynamic effects in cirrhotic patients with portal hypertension, see Albillos A, et al, *Hepatology*, 20(3): 611–617 (1994). -1-adrenergic agonists have been shown to precondition rabbit ischemic myocardium independent of adenosine by direct activation of protein kinase, see Tsuchida, et al, *Circ. Res.*, 75(3): 576–585 (1994).

Compounds which modulate -1-adrenergic subtype response have additionally been implicated as useful for treatment of conditions such as hypertension, see U.S. Pat. No. 4,440,769, ischemic heart disease, and psychoses, see Japanese Patent JP 03264579,congestive heart failure, see PCT application WO 92/00741, cerebral angiopathy, see Japanese Patent JP03264579, sympathetically maintained pain in peripheral tissues, see PCT application WO 92/14453 and 91/2806; allergies, hypolipemia, peripheral vascular disorders and glaucoma, see French Patent FR 2574401, thrombosis and asthma, see European Patent 62596, dysuria and pollakiuria, see Japanese Patent 03090027, bronchial spasms, hemorrhoids and nasal congestion, see South African Patent ZA 8502785.

Furthermore, -1-adrenergic subtypes have been shown to have a role in mediating adrenergic vasoconstiction in kidney of two kidney, one-clip Goldblatt and deoxycorticosterone acetate-salt hypertensive rats, see Sattar, et al, *J. Cardiovasc. Pharmacol.* 24(3), 420–428 (1994), to have analgesic potency after systemic administration in amphibians, see Brenner, et al, *J. Pharmacol, Exp. Ther.*, 270(2)., 540–545 (1994), to be involved in the effects of hippocampal vasopressinergic treatment on retrieval and relearning, see metzger, et al, *Behav. Neural. Biol.*, 62(2), 90–99 (1994), to have a role in sleep-wakefulness and body temperature regulation *Brain Res. Bull.*, 35(2), 171–177 (1994), to be involved with cardiac myocytes following coronary artery constriction in rats, see Cheng, et al, *Cardiovasc. Res.*, 28(7), 1070–1082 (1994), to mediate biochemical, molecular, and morphologic features of cultured myocardial cell hypertrophy, see *J. Biol. Chem.*, 268, 15374 (1993), to be involved with phasic and tonic vasoconstrictor responses, see Wong P. C. , et al, *Eur. J. Pharmacol;.*262(1–2):185–188 (1994), to have a role in human liver during intraabdominal sepsis, see Hwang T, et al, *Hepatology;* 20(3): 638–642 (1994), to modulate phosphatidylinositol cycle in cultured rat cardiomyocytes, see Van Heugten H, et al,*J. Mol. Cell Cardiol.* 26(8);1081–1093 (1994), and to be involved in glucose release and thus diabetes, see Capusso, A., et al, *Gen. Comp. Endocrinol.*, 95 (3), 457–463 (1994).

Piperazinyl oxazole compounds are known and have been described for use as anti-inflammatory, analgesic and antihistamine agents. Publications disclosing piperazinyl oxazoles representative of the compounds known in the art include a number of Mitsubishi Chemical Industry Japanese patent applications such as JA-0955423 (1977); JA-095919 (1977); JA-020326 (1976); JA-095422 (1977); and, JA-096385 (1977). The Institute Farmacologico Serona SpA. has published work with amino oxazole compounds and references disclosing such compounds are JA-4602020-0 (1971); and FR 1,538,009 (1996).

The oxazole compounds of the present invention selectively inhibit the -1c adrenergic receptor subtype and are therefore useful in the treatment of BPH and other obstructive conditions in which urination is difficult or strained.

SUMMARY OF THE INVENTION

Oxazole compounds useful as antagonists of -1C adrenoceptor of the following formula (I):

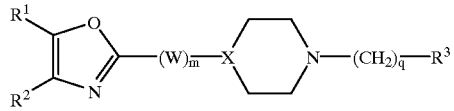

wherein:

$R^1$ and $R^3$ are selected from the group consisting of hydrogen, hydroxy, $C_{1-6}$alkyl, $C_{1-6}$alkoxy, $C_{1-6}$alkoxy$C_{1-6}$alkyl, phenyl or phenyl mono- or disubstituted with $C_{1-6}$alkyl, halogen, hydroxy, $C_{1-6}$alkoxy, aminosulfonyl, $C_{1-6}$alkylsulfonylamino $C_{1-6}$alkyl or carbamyl$C_{1-6}$alkylaminosulfonyl;

$R^2$ is selected from hydrogen, $C_{1-6}$alkyl, $C_{1-6}$alkoxy, hydroxy$C_{1-6}$alkyl, $C_{1-6}$alkoxy $C_{1-6}$alkyl or (fluorinated $C_{1-6}$alkyl)oxy $C_{1-6}$alkyl;

W is a $C_{1-6}$alkylene chain or nitrogen;

m is independently the integer 0 or 1;

X is CH or nitrogen, provided that when W is nitrogen then X is CH;

q is independently an integer selected from the group consisting of 1, 2, 3 or 4; when the proviso that when:

$R_1$ is phenyl or phenyl that is mono or disubstituted with halogen, methyl or methoxy;

$R_2$ is hydrogen or methyl, $R_3$ is hydrogen, hydroxy or $C_{1-6}$alkoxy;

q is 1, 2, 3 or 4,

W is (CH$_2$); and m is 1, then X will be CH;

or pharmaceutically acceptable acid-addition or base-addition salt thereof.

DETAILED DESCRIPTION OF THE INVENTION

This invention relates to novel alpha1c adrenoceptor binding compounds of the following formula (I):

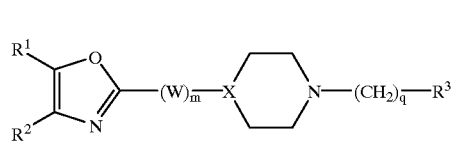

wherein:

$R^1$ and $R^3$ are selected from the group consisting of hydrogen, hydroxy, $C_{1-6}$alkyl, $C_{1-6}$alkoxy, $C_{1-6}$alkoxy$C_{1-6}$alkyl, phenyl or phenyl mono- or disubstituted with $C_{1-6}$alkyl, halogen, hydroxy, $C_{1-6}$alkoxy, aminosulfonyl, $C_{1-6}$alkylsulfonylamino$C_{1-6}$alkyl or carbamyl$C_{1-6}$alkylaminosulfonyl;

$R^2$ is selected from hydrogen, $C_{1-6}$, $C_{1-6}$alkoxy, hydroxy $C_{1-6}$alkyl, $C_{1-6}$alkoxy $C_{1-6}$alkyl or (fluorinated $C_{1-6}$alkyl) oxy $C_{1-6}$alkyl;

W is a $C_{1-6}$alkylene chain or nitrogen;

m is independently the integer 0 or 1;

X is CH or nitrogen, provided that when W is nitrogen then X is CH;

q is independently an integer selected from the group consisting of 1, 2, 3 or 4; with the proviso that when:

$R_1$ is phenyl or phenyl that is mono or disubstituted with halogen, methyl or methoxy;

$R_2$ is hydrogen or methyl, $R_3$ is hydrogen, hydroxy or $C_{1-6}$ alkoxy;

q is 1, 2, 3 or 4,

W is (CH$_2$); and m is 1, then X will be CH;

or pharmaceutically acceptable acid-addition or base-addition salt thereof.

in particular, the present invention is directed to compounds of formula (I) where:

1. $R^1$ and $R^3$ are selected from the group consisting of phenyl or phenyl mono or disubstituted with $C_{1-6}$alkyl, halogen, hydroxy, $C_{1-6}$alkoxy, aminosulfonyl, $C_{1-6}$alkylsulfonylamino$C_{1-6}$alkyl or carbamyl$C_{1-6}$alkylaminosulfonyl;
2. $R^3$ is phenyl mono or disubstituted with hydroxy, $C_{1-6}$alkoxy, aminosulfonyl, $C_{1-6}$alkylsulfonylamino$C_{1-6}$alkyl or carbamyl$C_{1-6}$alkylaminosulfonyl;
3. $R^3$ is phenyl disubstituted with methoxy and carbamyl $C_{1-6}$alkylaminosulfonyl;
4. $R^3$ is phenyl disubstituted with methoxy and aminosulfonyl;
5. $R^1$ phenyl or phenyl mono or disubstituted with halogen; $R^3$ is phenyl mono or disubstituted with hydroxy, $C_{1-6}$alkoxy, aminosulfonyl, $C_{1-6}$alkylsulfonylamino$C_{1-6}$alkyl or carbamyl$C_{1-6}$alkylaminosulfonyl;
6. $R^3$ is phenyl substituted with methoxy;
7. $R^3$ is (3-carbamyl$C_{1-6}$alkylaminosulfonyl-4-methoxy) phenyl;
8. $R^3$ is phenyl disubstituted with $C_{1-3}$alkoxy and $C_{1-6}$alkylaminocarbonyl $c_{1-6}$alkylaminosulfonyl;
9. $R^3$ is (3-aminosulfonyl-4-methoxy)phenyl;
10. $R^3$ is hydroxy;
11. $R^2$ is (fluorinated$C_{1-6}$alkyl)oxy$C_{1-6}$alkyl;
12. $R^2$ is 2,2,2-trifluoroethoxymethyl;
13. $R^2$ is $C_{1-6}$alkyl;

14. $R^2$ is hydrogen;
15. $R^1$ is phenyl or phenyl mono or disubstituted with halogen;
16. $R^1$ is phenyl or phenyl mono or disubstituted with fluorine;
17. $R^1$ is phenyl mono or disubstituted with fluorine;
18. $R^1$ is phenyl;
19. $R^1$ is phenyl mono or disubstituted with chlorine;
20. $R^1$ is phenyl mono or disubstituted with fluorine; $R^2$ is (fluorinated$C_{1-6}$alkyl)oxy$C_{1-6}$alkyl; $R^3$ is phenyl disubstituted with methoxy and carbamyl$C_{1-6}$alkylaminosulfonyl or methoxy and aminosulfonyl;
21. X is CH;
22. q is 2;
23. m is 0;
24. $R^3$ is 4-hydroxy or $C_{1-6}$alkoxyphenyl optionally substituted in the meta-position by aminosulfonyl or carbamyl$C_{1-6}$alkylaminosulfonyl;
25. $R^3$ is 4-hydroxy or methoxyphenyl optionally substituted in the meta position by aminosulfonyl or carbamylmethylaminosulfonyl;
26. $R^2$ is hydrogen, hydroxy$C_{1-6}$alkyl, $C_{1-6}$alkoxy$C_{1-6}$alkyl, or (fluorinated $C_{1-6}$alkyl)oxy$C_{1-6}$alkyl;
27. $R^2$ is $C_{1-6}$alkoxy$C_{1-6}$alkyl or (fluorinated $C_{1-6}$alkyl)oxy$C_{1-6}$alkyl;
28. $R^2$ is ethoxymethyl or 2,2,2-trifluoroethoxymethyl.

Fluorinated alkyl in more detail is an alkyl wherein one or more of the hydrogen atoms is replaced by a fluorine atom; $C_{1-6}$alkyl refers to methyl, ethyl, propyl, butyl, pentyl and hexyl; and halogen refers to chlorine, fluorine, bromine and iodine. Particular alkyl groups are those containing 1–4 carbon atoms.

Suitable pharmaceutically acceptable salts of the compounds of formula (I) include acid addition salts formed with acids, e.g. hydrochlorides, hydrobromides, sulfates, alkyl- or arylsulfonates, phosphates, acetates, citrates, succinates, lactates, tartrates, fumarates, and maleates; and base salts such as alkali metal salts e.g. sodium salts.

Other salts which are not pharmaceutically acceptable may be useful in the preparation of compounds of formula (I) and these form a further aspect of the invention.

Solvates of compounds of formula (I) are also within the scope of the present invention. Solvates can be formed by the reaction of organic compounds with solvents in which they are reacted or from which they are precipitated or crystallized. The solvents of compounds according to formula (I) may, for example, be hydrates.

Compounds of the present invention can exist in more than one crystalline form. For example, crystalline forms may vary from solvate to solvate. Compounds of the present invention encompass all possible crystalline forms. In particular, for example, 5-(2-{4-[5-(4-fluorophenyl)-4-(2,2,2-trifluoroethoxymethyl)-oxazol-2-yl}-ethyl)-2-methoxybenzenesulfonamide hydrochloride exists in four known crystal forms. Form I melts around 145° C. and converts to Form III which has a melting point around 200° C. At room temperature, both Form I and Form III convert to a hydrated form (Form IV) in aqueous media. The hydrate (stoichiometry unknown) readily converts to an anhydrous form (Form II) upon separation from the aqueous media. Form II converts to form IV at greater then 70% relative humidity. Below 70% relative humidity, Form II is non-hydgroscopic and shows good solid state and chemical stability.

The present invention encompasses the individual enantiomers of the compounds represented by formula (I) above as well as wholly or partially racemic mixtures thereof. The present invention also covers the individual enantiomers of the compounds represented by formula (I) above as mixtures with diastereoisomers thereof in which one or more of the two sterocenters is inverted.

Metabolites of compounds of formula (I) are also within the scope of the present invention. Metabolites of compounds of formula (I) may be, for example, those where $R^1$ is 4-fluorophenyl, $R^2$ is individually methoxy, 2,2,2 trifluoroethoxymethyl or methoxymethyl and $R^3$ is a phenyl group substituted with both an aminosulfonyl moiety and either a hydroxy or $C_{1-6}$alkoxy moiety.

Appropriate amounts of compounds according to the present invention may be administered to a patient to treat disorders which include benign prostatic hyperplasia ("BPH"), cardiac arrhythmia, glaucoma, male pattern baldness and hypertension. In particular, compounds of the present invention selectively inhibit the -1c adrenergic receptor subtype and are therefore useful in the treatment of BPH and other obstructive conditions in which urination is difficult or strained.

It will be appreciated that reference to treatment is intended to include prophylaxis as well as the alleviation of established symptoms.

General Chemistry Procedures

Compounds of general formula (I) may be prepared by methods known in the art of organic synthesis, as shown in part by the following processes and schemes. For any of these processes and schemes, it may be necessary and/or desirable to protect sensitive or reactive groups. Protecting groups are employed according to standard methods of organic synthesis (T. W. Green and P. G. M. Watts (1991) *Protecting Groups in Organic Synthesis*, John Wiley & Sons). These groups are removed at a convenient stage of synthesis using methods known from the art. Thus, for example, amino groups may be protected by a group selected from aralkyl (e.g. benzyl), acyl, or sulfonyl, e.g. allylsulfonyl, phthalimide, or tosyl; subsequent removal of the protecting group being effected when desired by hydrolysis or hydrogenolysis as appropriate using standard conditions. Hydroxyl and carboxyl groups may be protected using any conventional hydroxyl or carboxyl protecting group. Examples of suitable hydroxyl and carboxyl protecting groups include groups selected from alkyl, e.g. methyl, tert-butyl, or methoxymethyl, aralkyl, e.g. benzyl, diphenylmethyl, or triphenylmethyl, heterocyclic groups such as tetrahydropyranyl, acyl, e.g. acetyl or benzoyl, and silyl groups such as trialkylsilyl, e.g. tert-butyldimethylsilyl. The hydroxyl protecting groups may be removed by conventional techniques. Thus, for example, alkyl, silyl, acyl, and heterocyclic groups such as triphenylmethyl may similarly be removed by hydrolysis under acidic conditions. Aralkyl groups such as benzyl may be cleaved by hydrogenolysis in the presence of a noble metal catalyst such as palladium-on-charcoal. Silyl groups may also conveniently be removed using a source of fluoride ions such as tetra-n-butylammonium fluoride.

As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification: g (grams); mg (milligrams); L (liters); mL (milliliters); psi (pounds per square inch); M (molar); mM (millimolar); i.v. (intravenous); Hz (Hertz); mol (moles); RT (room temperature); min (minutes); h (hours); m.p. (melting point); TLC (thin layer chromatography); MeOH (methanol); TFA (trifluoroacetic acid); THF (tetrahydrofuran); dimethylsulfoxide (DMSO); EtOAc (ethyl acetate); dichloromethane (DCM); dimethylformamide (DMF); 1,1-carbonyldiimidazole (CDI); isobutylchloroformate (iBuCF); N-hydroxysuccinimide (HOSu); N-hydroxybenztriazole (HOBT); 1-(3-dimethylaminopropyl)-3-ethylcarbodiimide hydrochloride (EDC); bis(2-oxo-3-oxazolidinyl) phosphinic chloride (BOP); tert-butyloxycarbonyl-1-yl-oxy-tris(dimethylamino)-phosphonium hexafluorophosphate (BOP); bromo-tris-pyrrolidino-phosphonium hexafluorophosphate (PyBrop). BOP and PyBrop are both available from NovaBiochem, San Diego, Calif. All references to ether are to diethyl ether. Unless otherwise indicated, all temperatures are expressed in °C. (degress Centigrade). All reactions conducted at room temperature unless otherwise noted.

The $^1$HNMR spectra were recorded on either a Varian (VXR-300 or a Varian Unity-300 instrument. Chemical shifts are expressed in parts per million (ppm, D units). Coupling constants are in units of hertz (Hz). Splitting patterns are designated as s, singlet; d, doublet; t, triplet; q, quartet; m, multiplet; b, broad.

Low-resolution mass spectra (MS) were recorded on a JOEL JMS-AX505HA, JOEL SX-102 or a SCIEX-APIiii spectrometers. All mass spectra were taken in the positive ion mode under electrospray ionizatin (ESI), chemical ionization (CI), electron impact (EI) or by fast atom bombardment (FAB) methods. Infrared (IR) spectra were obtained on a Nicolet 510 FT-IR spectrometer using a 1-mm NaCI cell. Rotations were recorded on a Perkin-Elmer 241 polarimeter. All reactions were monitored by thin-layer chromatography on 0.25 mm E. Merck silica gel plates (60F-254), visualized with UV light, 7% ethanolic phosphomolybdic acid, p-anisldehyde solution or iodine. Flash column chromatography was performed on silica gel (230–400 mesh, Merck).

Products were purified by preparative reversed phase high pressure liquid chromatography (RP-HPLC) using a Waters Model 3000 Delta Prep equipped with a Delta-pak radial compression cartridge ($C_{18}$, 300 A, 15 m, 47 mm×300 mm). Linear gradients were used in all cases and the flow rate was approximately 100 mL/minute ($t_0$=5.0 min). All solvents contained 0.1% TFA. Analytical purity was assessed by RP-HPLC using a Waters 600E system equipped with a Waters 990 diode array spectrometer (I range 200–400 nM). The stationary phase was a Vydac $C_{18}$ column (5 m, 4.6 mm×250 mm). The flow rate was 1.0 to 1.5 ml/min. ($t_0$=2.8 or 3.0 min.) and the solvent systems were as described above. Data reported as tr, retention time in minutes (% acetonitrile over time).

For the following Schemes $R^1$, $R^2$, $R^3$, W, m, X and q are defined as for formula (I) above.

According to scheme 1, compounds of type (1a) are coupled with compounds of type 1b where PG represents a nitrogen protecting group such as aralkyl (e.g. benzyl), acyl or sulfonyl (e.g. alkylsulfonyl, phthalimide or tosyl), using an appropriate coupling reagent to form an amide bond and give compounds of type (1c). Appropriate coupling reagents include, but are not limited to, carbonyl diimidazole, N,N'-dicyclohexylcarbodiimide, BOP reagent, and PyBrop. Compounds of type 1c may be then cyclized by warming in an appropriate reagent (e.g. $H_2SO_4$, $SOCl_2$, TFA) to give compounds of structure 1d.

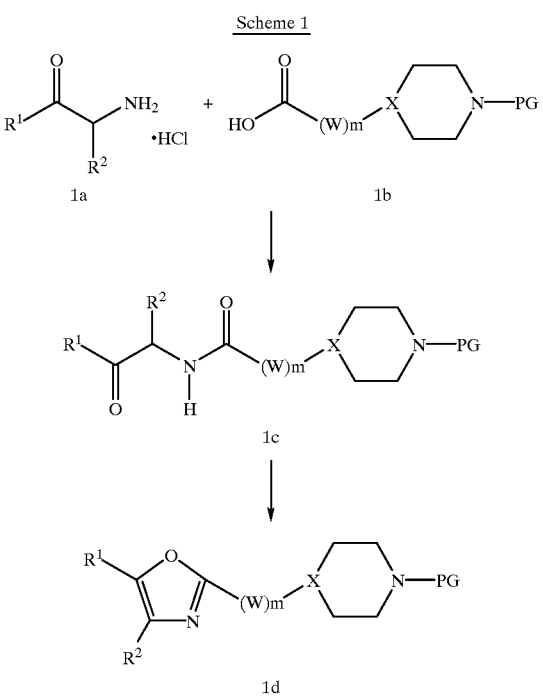

Alternatively, compounds of type (1d) may be made by the process outlined in Scheme 2. Compounds of type (2a), where LG represents a leaving group such as Cl, Br, or I, are reacted with compounds of type 1b to give esters of type (2b). Compounds of type (2b) may be cyclized to compounds of type 1d by heating in an appropriate solvent (e.g. acetic acid) with ammonium acetate.

Scheme 2

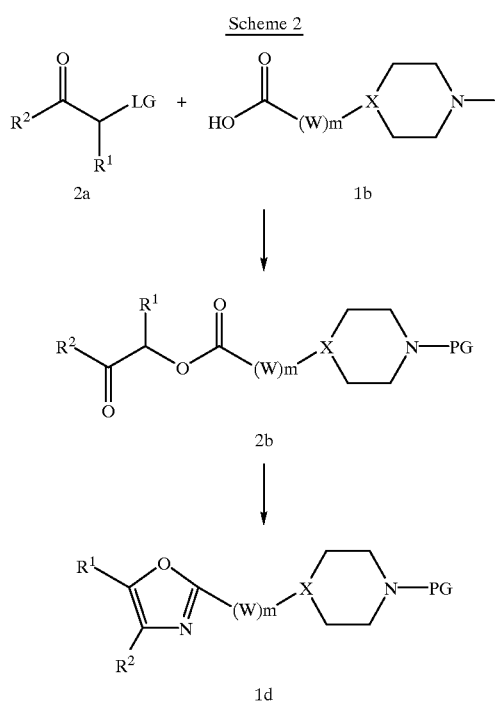

Another process by which compounds of type (1d) may be made is outlined in Scheme 3. Compounds of type 1a may be converted into compounds of type (3a) by reaction with carbon disulfide in an appropriate solvent (e.g. EtOH /H$_2$O mixture) in the presence of a suitable base (eg Na$_2$CO$_3$). Compounds of general formula 3a may be converted to compounds of type (3b) by reaction with an appropriate chlorinating agent (e.g. POCl$_3$). Reaction of compounds of the type (3b) with appropriate compounds of the type 3c (W=N, or if m=0, then X=N) at elevated temperatures in a suitable solvent affords compounds of the type (1d).

Scheme 3

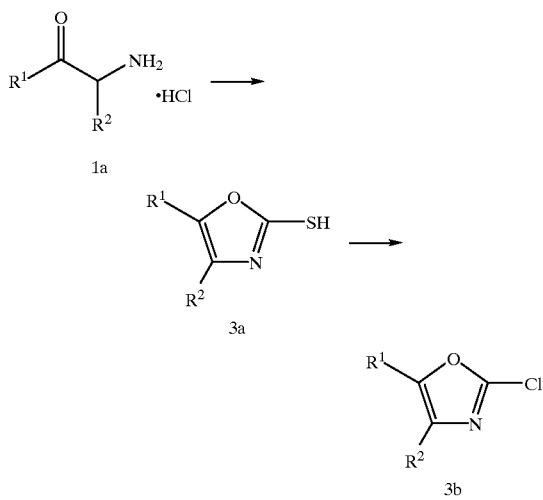

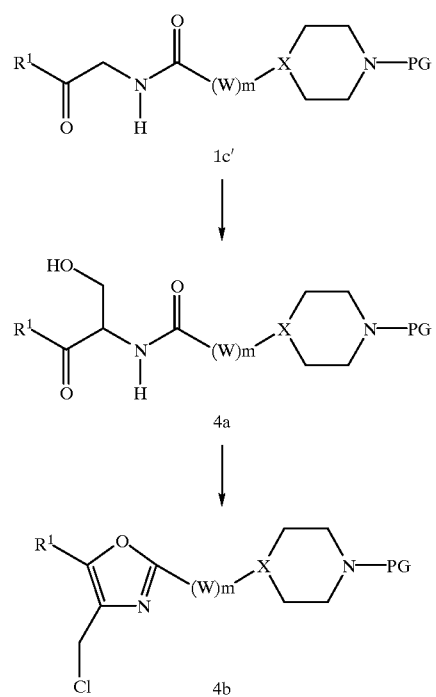

Compounds of type (1c'), made as in the first step of scheme 1, may be hydroxymethylated to give compounds of type (4a) by use of an appropriate formaldehyde source (e.g. aqueous formaldehyde) and an appropriate base (e.g. NaHCO$_3$) in a suitable solvent (e.g. EtOH /H$_2$O mixtures). Compound of the type (4a) can be cyclized to compounds of type 4b by warming with SOCl$_2$, as outlined in Scheme 4.

Scheme 4

Compounds of type (4b) could be transformed into compounds of type 5c and 5d by the process described in Scheme 5. Hydrolysis of compounds (4b) with a suitable base in a suitable solvent gives compounds of type (5a). Oxidation by an appropriate method (e.g. Swern oxidation) affords compounds of type (5b). Compounds (5b) may be reacted with an appropriate Wittig or Horner-Emmons reagent to afford olefins of type (5c). If desired, saturated compounds of type (5d) may be obtained by reduction of compounds (5c) using an appropriate reduction method (e.g.

10% Pd/C, 50 psi H$_2$). R$^8$ is selected from the group consisting of hydrogen, C$_{1-6}$alkoxy or (fluorinatedC$_{1-6}$alkyl)oxyl.

wherein R$^5$ is C$_{1-6}$alkyl, with chloromethyl compounds of type (4b) in an appropriate solvent (e.g. THF) gives compounds of type (7a).

Scheme 5

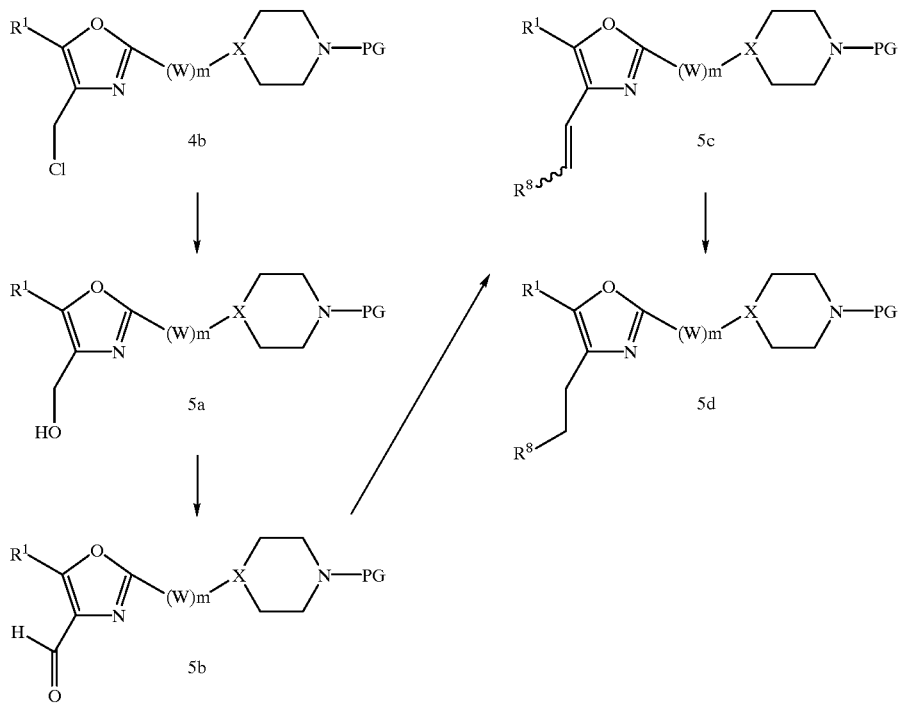

Compounds of type (6a) are available from compounds of type (4b) by heating with an alcohol R$^5$OH and NaOH wherein R$^5$ is C$_{1-6}$alkyl. This process, depicted in Scheme 6 serves both to displace the chlorine and remove the nitrogen protecting group.

Scheme 6

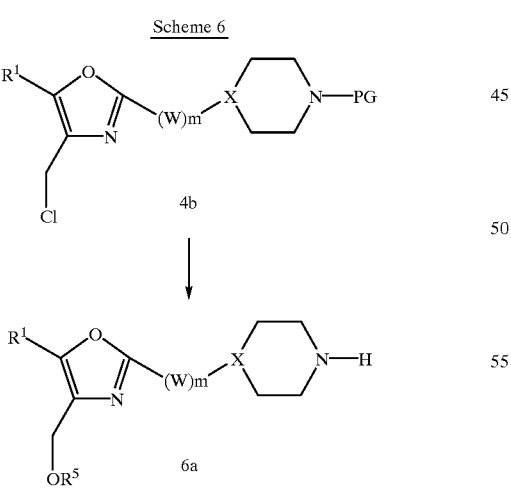

Compounds of type (7a) may be made by the process shown in Scheme 7. These compounds are similar to compounds 6a, but the nitrogen retains the protecting group. Reaction of the alkoxide (prepared by standard methods using a suitable base such as NaH or lithium bistrimethylsilylamide) of an appropriate alcohol R$^5$OH, Scheme 7

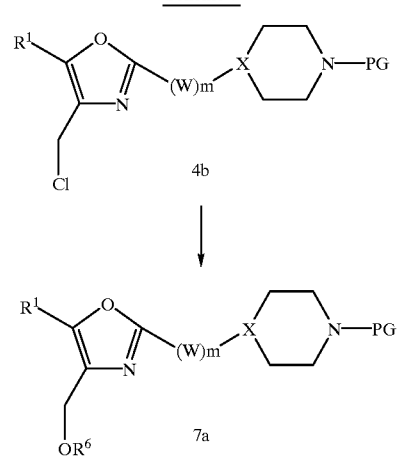

Scheme 8 depicts the process of removal of the protecting group from nitrogen from compounds of the type 1d to afford compounds of type (8a). Compounds of type (5c), (5d), and (7a) are subsets of compound 1d. Removal of the nitrogen protecting group may be accomplished, for example, by a method found in *Protective Groups in Organic Synthesis*, supra.

Scheme 8

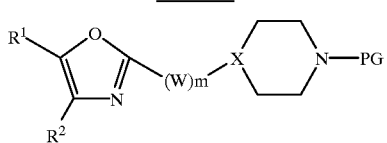

1d (or 5c, 5d, 7a)

↓

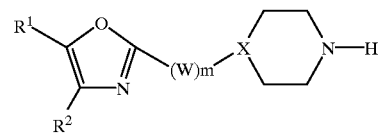

8a

Scheme 9 and 10 depict processes for synthesizing alkylating agents which may be used to alkylate the nitrogen atom of compounds represented by (8a). Reaction of chlorosulfonic acid in a suitable solvent (e.g. $CH_2Cl_2$) with compounds such as (9a) gives sulfonyl chlorides such as (9a). These sulfonyl chlorides may be reacted with an appropriate amine in a suitable solvent (e.g. 1,4-dioxane) with a base present (e.g. diisopropylethylamine) to afford compounds of type (9c). Compounds of type (10c) may be prepared by converting the hydroxyl group of Compounds (10b) into a suitable leaving group (e.g. tosylate, mesylate, Cl, Br) by standard chemistry known by one skilled in the art. Compounds of type (10b) may be prepared from compounds of type (10a) by a suitable reduction procedure. $R^6$ is $C_{1-6}$alkyl. $R^7$ and $R^8$ are selected from the group of any amino substituents found on an amino definition within the substituted phenyl definition for formula (I).

Scheme 9

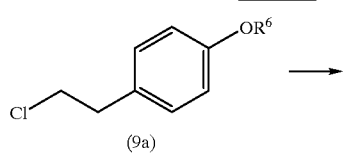
(9a)

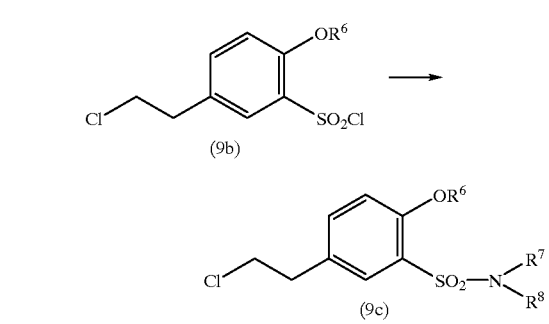

Scheme 10

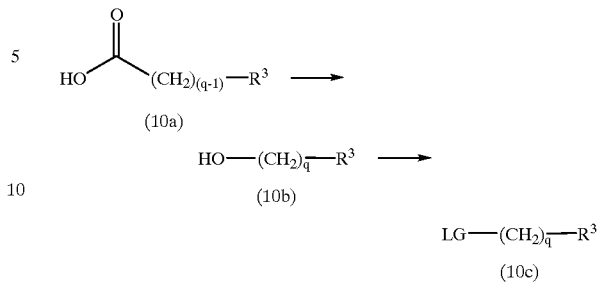

Finally, oxazole compounds of the formula (I) may be prepared by general process (A) from the reaction of compounds of formula (8a) (includes compounds of formula (6a)) or salts thereof with compounds of formula (10c), (includes compounds of formula (9c)).

Scheme 11

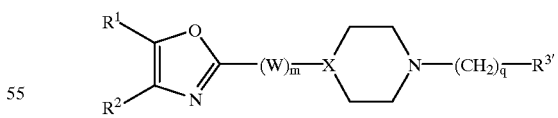

8a (includes 6a)

↓

Typically, the reaction may be carried out in a suitable solvent (e.g. DMF, ethanol, $CH_3N$, 1,4-dioxane), and a base (e.g. diisopropylethylamine, potassium carbonate) at elevated temperatures (e.g. 50–200° C.), optionally in the presence of an additive (e.g. LiBr, NaI), as depicted in Scheme 11.

According to another general process (B), a compound of formula (I) wherein $R^3$ is phenyl substituted with at least one $C_{1-6}$alkylsulfonylamino$C_{1-6}$alkyl group may be prepared by reacting a compound of formula (II)

wherein $R^{3'}$ is phenyl substituted with at least one amino$C_{1-6}$alkyl group, or a salt thereof with a reagent serving to introduce a $C_{1-6}$alkylsulfonyl group. Suitable sulfonylating agents include sulfonyl chlorides e.g. methanesulfonylchloride.

According to another general process (C), a compound of formula (I) according to the invention may be converted into another compound of the invention using conventional procedures.

Thus, for example a compound of formula (I) wherein one or more of $R^1$ and $R^3$ represent a mono or di-substituted phenyl group may be prepared from a corresponding compound of formula (I) wherein one or more of $R^1$ and $R^3$ represent phenyl or a mono-substituted phenyl group, using conventional techniques.

According to another general process (D), a compound of formula (I) according to the invention, or a salt thereof may be prepared by subjecting a protected derivative of formula (I) or a salt thereof to reaction to remove the protecting group or groups.

Thus, at an earlier stage in the preparation of a compound of formula (I) or a salt thereof it may have been necessary and/or desirable to protect one or more sensitive groups in the molecule to prevent undesirable side reactions.

As will be appreciated, in any of the general processes (A) to (C) described above it may be necessary or desired to protect any sensitive groups in the molecule as just described. Thus, a reaction step involving deprotection of a protected derivative of general formula (I) or a salt thereof may be carried out subsequent to any one of the above described processes (A) to (C).

Thus, according to a further aspect of the invention, the following reactions may, if necessary and/or desired be carried out in any appropriate sequence subsequent to any of the processes (A) to (C).

(i) removal of any protecting groups; and
(ii) conversion of a compound of formula (I) or a salt thereof into a pharmaceutically acceptable salt thereof.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

Pharmacology

The efficacy of compounds of the present invention can be evaluated and measured using pharmacological methods known in the art or as described in detail below based on similarly established methodologies.

1. HUMAN -1B, -1C AND -1D RECEPTOR BINDING ASSAYS

REFERENCES

1. Cheng, Y. C. and Prusoff, W. H. Relationship between the inhibition constant (Ki) and the concentration of inhibitor which causes 50% inhibition of an enzymatic reaction. Biochem. Pharmacol. 22:3099-3108 (1973).
2. Lutz, M. W., Goetz, A. S., Morgan, P. H. and Rimele T. J. Statistical and graphical methods for analysis of radioligand binding experiments: Development of a RS/1 based tool palette. Proc. of BBN worldwide user meeting, p. 26 (1991).

Method

Binding studies were performed in 96 well microtiter plates incubated at 25 degrees C for 90 min. Incubations (222 $\mu$l) contained 0.5 $\mu$g of protein, in a buffer consisting of 25 mM PIPES, 150 mM NaCl, 5 mM $MgCl_2$, mM EDTA, pH 7.5 (assay buffer), approximately 75,000 cpm (70 pM) of [125I]-HEAT, and displacing ligands or vehicle (3.0% DMSO/25 mM HOAc in $H_2O$, 0.3%/2.5 mM final concentration in assay) as appropriate. The reaction was terminated by rapid vacuum filtration through GF/B glass fiber filters, presoaked in 0.1% BSA for 30 min., using a Brandel cell harvester. The filters were washed with approximately 4 ml ice cold 25 mM Tris-HCL, pH=7.4 buffer. Retained radioactivity was determined by gamma counting in a LKB gamma counter. Nonspecific binding was determined in the presence of 100 $\mu$M phentolamine and usually<=15% of total binding.

Materials

Cell Culture:

Rat-1 fibroblast cells expressing adrenergic receptor subtype were developed at Glaxo. Dulbecco's Modified Eagles Medium (D-MEM), trypsin-EDTA, penicillin/streptomycin, geneticin were purchased from Gibco (Grand Island, N.Y.). Fetal bovine serum was purchased from Hyclone (Logan, Utah).

Compounds

Phentolamine, albumin, bovine fraction V, were purchased from Sigma(St. Louis, Mo.); 5-$CH_3$-urapidil was purchased from Research Biochemicals incorporated (Natick, Mass.).

Radioligand

[125I]I-HEAT, specific activity 2200 Ci/mmol was purchased from New England Nuclear (Wilmington, Del.).

PROCEDURE

Preparation of the Test Compound

1. Dissolve compound in distilled water or dimethylsulfoxide according to solubility.
2. When a solvent is used, estimate the solvent effects on binding. Use a concentration that does not affect binding.

Preparation of Cell Membrane

1. Adherent rat-1 fibroblast cells expressing alpha-1 adrenergic receptors were grown to 80–90% confluency in roller bottles, in D-MEM supplemented with 5% fetal bovine serum, penicillin/streptomycin (10 unit/10 ug/ml) and geneticin (500 ug/ml).
2. Cells were removed from flasks using trypsin/EDTA, washed in pbs, pelleted, washed and quick frozen on dry ice/EtOH. Cells were stored in −80 degrees C until needed.

*The following procedures were performed at 4 degrees C unless otherwise stated.

3. Frozen aliquots of cells were thawed at room temperature and suspended 50 mM Tris-HCL, 250 mM sucrose buffer, pH=7.4, containing 1 ug/ml aprotinin, 17 ug/ml PMSF, 20 ug/ml bacitracin, 1 mM benzamidine, 10 ug/ml leupeptin and 10 ug/ml pepstatin A.
4. The cells were disrupted using a Tekmar tissuemizer, setting 5 for 30 seconds, then homogenized in a dounce homogenizer by 10 strokes with a tight fitting pestle.
5. The homogenate was centrifuged at 100,000×g for 30 min. (Sorvall F28/36 rotor, 28,000 RPM).
6. The resulting pellet was resuspended in centrifugation buffer (10 mM Tris-HCl, pH 7.4), homogenized and centrifuged as previously described.
7. The pellets were collected, suspended in centrifugation buffer and protein concentration was determined by BIO-RAD. Bovine serum albumin was used as the standard.
8. Aliquots were stored at −80 degrees C until assayed. Binding was stable for at least 6 months under these storage conditions.

Performing the Experiment

1. Binding studies were performed in 96 well microliter plate at 25 degrees C incubated for 90 min.
2. Incubations (222 μl) contained 0.5 μg of protein, in a buffer consisting of 25 mM PIPES, 150 mM NaCl, 10 mM $MgCl_2$, 1 mM EDTA, pH 7.5 (assay buffer).
3. Approximately 75,000 cpm (70 pM) of [125I]l-HEAT, and displacing ligands or vehicle (3.0% DMSO/25 mM HOAc in $H_2O$, 0.3%/2.5 mM final concentration in assay) as appropriate.
4. The reaction was terminated by rapid vacuum filtration through GF/B glass fiber filters, presoaked in 0.1% BSA for 30 min., using a Brandel cell harvester.
5. The filters were washed with approximately 4 ml ice cold 25 mM Tris-HCL, pH=7.4 buffer and punched into tubes.

DATA COLLECTION AND ANALYSIS

Collecting the Data

Retained radioactivity (in filter) was determined by gamma scintillation counting as total binding. Specific binding is determined by subtracting the non-specific binding from the total binding and subsequently processed by RADLIG.

Calculating the PKI

The IC50 represents the concentration of inhibitor giving 50% decrease of binding relative to control. Ki values were calculated by the method of Cheng and Prusoff. (1) The pKi is the -log of the Ki (inhibition constant). The Ki is also termed a compound's affinity for the receptor.

1. Competition curves were fit to models of ligand binding to single and multiple receptor sites implemented in the RS/1 (BNN Software Products, Cambridge Mass., version 4.2) statistical analysis program called RADLIG. (2)
2. A partial F-test was used to discriminate between one and two site models.
3. The Ki is calculated from the fit of the curve to a single receptor site if the Hill coefficient (N) is not statistically different from unity (constrained model). If the Hill coefficient is greater then unity, the Ki is calculated from the fit of the curve to the unconstrained model. If the Hill coefficient is less than unity and a multiple receptor site model is a significantly better fit, the Ki is calculated from the fit of the curve to a multiple receptor site and multiple Kis are calculated.

TABLE 1

Relative Functional Receptor Binding Activity

| Example Number | Human -1B | Human -1C | Human -1D |
|---|---|---|---|
| 1 | ++ | +++ | ++ |
| 2 | ++ | +++ | ++ |
| 3 | ++ | +++ | ++ |
| 4 | ++ | +++ | ++ |
| 5 | ++ | +++ | ++ |
| 6 | ++ | +++ | ++ |
| 7 | ++ | +++ | ++ |
| 8 | ++ | +++ | ++ |
| 12 | ++ | +++ | +++ |

2. TISSUE ARRAYS

A. CANINE URETHRAL-PROSTATE PRESSURE

Purpose

To evaluate the ability of compounds to affect urethral-prostate pressure (contractility) while assessing their cardiovascular effects simultaneously.

Method

Using hypogastric nerve stimulation (NS) and the −1 agonist phenylephrine (or other receptor agonists, as appropriate) the responses of urethral pressures and systemic blood pressure are recorded. The tests compounds are then given in a log dose infusion. The inhibition of the NS response within the prostate as well as the systemic phenylephrine response on blood pressure is measured to assess the uro-selectivity of the compound in the anesthetized dog.

Interpretation

Interesting compounds are those that express uro-selectivity with a ratio of >100 for the urethral pressure vs diastolic blood pressure comparisons (BP.US).

Detailed Description

MATERIALS

Species

Male mongrel dogs (10–20 kg)

Anesthesia

1. Nembutal (pentobarbital sodium) 50 mg/ml, Abbott Laboratories.
2. Barbital (sodium salt) No. B-0500, Sigma Chemicals.

LABORATORY CHEMICALS AND SOLUTIONS

Phenylephrine Hydrochloride Injection (1%), Schein.
Compound Vehicle Solution
0.05 N HCL in distilled water.

Bladder Perfusion Solution
Sodium Chloride 0.9% (L8000), Kendall-McGraw Labs.
IV Flush Solution
Isotonic Saline (Cat B3158-1), Baxter Health Care.
Heparin Sodium
1000 u/ml, Elkins Sinn Inc.

General Laboratory Equipment

Urethral Catheter Size 8 Fr×16" HRI 8890 700811, Sovereign.
Harvard Ventilator Model 613, Harvard Apparatus.
IL 1306 Blood Gas Analyzer, Instumentation Laboratories.
Surgistat Model B Electro cautery, Valley Labs.
Model K20 Heating pad, Baxter Health Care.
Grass Stimulator Model S887E
Harvard Dastre Electrode #50-6873

Recording Equipment

Gould 3800S Physiograph
Micro Model MP15D Transducer
Modular Instruments Inc. On-line data acquisition system

PROCEDURE

Preparation of the Test Compound

1. Dissolve compound in a 0.05 N HCL (50 ml of 1 N of HCL in 1 L of distilled water).
2. Depending on drug solubility addition of heat may be necessary (temp as high as 60° C.).
3. All doses are to be given on a μg/kg (salt) dose.

Preparation of Alpha Agonist

1. Phenylephrine 1% solution (10 mg/ml), 1 ml to 250 ml of isotonic saline (40 μg/ml), bolus dose 10 μg/kg (salt).

Preparation of the Anesthetized Dog

1. Animals are given a combination of Na-pentobarbital (15 mg/kg) and Na-barbital (300 mg/kg) IV. intubated with a cuffed endotracheal tube and placed on a ventilator (Harvard Apparatus, model 613, South Natick, Mass. with room air).
2. Ventilation parameters are adjusted to maintain normal arterial blood gases. Standard settings are 12–24 respirators per minute and tidal volumes of 12–15 ml per kg.
3. A continuous infusion of pentobarbital is maintained throughout the duration of the experiment (3 mg/kg/hr).
4. Rectal temperature is monitored and maintained at 37–39° C. with a heating pad.
5. The femoral artery and vein are cannulated for blood pressure monitoring and infusion of drugs for anesthesia. The cephalic vein which is used for initial anesthesia induction is now used for the phenylephrine IV bolus injection.

ATTACHING THE ELECTRODE AND INSERTING THE CATHETER

1. A midline laparotomy is used to open the abdomen, and the hypogastric nerves are isolated from surrounding tissue and sectioned approximately 1 cm distal to the inferior mesenteric ganglion.
2. A bipolar electrode is then attached to the distal end of the ligated nerve. Using the same incision the bladder, prostate and the urethra are identified. The bladder is incised in the dome and two catheters are inserted through the bladder. One catheter is used for urine drainage and the other inserted antegrade into the proststic urethra. One suture is tied around the urethra distal to the prostate and another ligature secured proximally, around the bladder neck without occluding the ureters. A third suture is placed around both catheters at the bladder dome to stabilize preparation and allow urine to be collected externally.
3. The baseline pressure within the prostate is then adjusted to a level of 15 to 20 mmHg by addition of normal saline into the catheter. All incisions are then closed. The effects of either nerve stimulation (NS) or IV phenylephrine can be evaluated.

PERFORMING THE EXPERIMENT

1. After a control period of at least 30 minutes and establishment of stable baselines of urethral and blood pressure are observed, the control responses to NS or phenylephrine bolus are recorded.
2. A hypogastric nerve stimulation of 16 Hertz, 10 Volts, 10 msec pulse width and 10 sec train duration are given and changes in urethral pressures are recorded.
3. At a time point 5 minutes post NS a phenylephrine bolus (10 μg/kg) is given into the cephalic vein and changes in blood pressure are recorded. At least two NS and phenylephrine injections are performed and evaluated for their consistency, the second consistent stimulation is picked for the baseline value response.
4. The test compound is then administered in a cumulative log dose infusion in the femoral vein (0.1 ml/kg/min) over 5 min. Doses of antagonist and dual stimulations are alternative at 10 and 15-min intervals until the highest dose of the antagonist is administered, usually 0.3–1.0 mg/kg. The effect of the antagonist on both the baseline systemic and urethral pressures as well we the % inhibition of the NS and phenylephrine responses is recorded.

DATA COLLECTIONS AND ANALYSIS

The data is collected in three forms, raw data sheets, polygraph recording paper and on-line data acquisition system files. The pressure determinations are made from the graphics mode created form the Modular Instruments computer system. This method allows more precise measurements to be made because of the faster sampling times of the pressure curves. The data is then transferred to RS1 tables and graphs. The determination of the urethral and blood pressure values are calculated from a RS1 program for best curve fitting. From these curves the following measures are calculated:

UP ED50 (μg/kg): The dose of the test compound (salt) which produces 50% inhibition of the NS (nerve stimulation) response on urethral pressure.

BP ED50 (μg/kg): The dose of the test compound (salt) which produces 50% inhibition of the agonist response on diastolic blood pressure.

BP/UP: The ration of the BP ED50 to the UP ED50.

DBP-ED25 (μg/kg): The dose of the test compound (salt) which produces 25% inhibition of the agonist response on diastolic blood pressure.

UP-ED80 (µg/kg): The dose of the test compound (salt) which produces 80% inhibition of the NS (serve stimulation) response on urethral pressure.

%I-DBP: The percent inhibition of the diastolic blood pressure at the dose producing 80% inhibition of urethral pressure.

%Dec BP: The percent decrease of diastolic blood pressure at the dose producing 80% inhibition of the urethral pressure.

ED20BP (µg/kg): The dose of the test compound (salt) that decreases the diastolic blood pressure 20 mmHg from the baseline value.

The compound of Example 12 provided with the following tissue assay data:

UP ED50 13 µg/kg; BP ED50 7150 µg/kg; BP/UP=550.

The compound of Example 13 was administered at 10 mg/kg (po) to male Wistar rats. Slight to moderate ptosis was observed at between 1 and 4 hours after dosing. No other effects on behaviour, skeletal muscle tone, reflexes or respiration rate and no overt autonomic, gastrointestinal or neurological effects were observed and all animals appeared normal by 24 hours after dosing.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a physiologically acceptable salt or solvate thereof together with one or more pharmaceutically acceptable carriers or excipients. The carrier(s) or excipient(s) must be acceptable in the sense of being compatable with the other ingredients of the formulation and not deleterious to the recipient thereof. According to another aspect of the invention, there is provided a process for the preparation of a pharmaceutical formulation comprising admixing a compound of formula (I) or a pharmaceutically acceptable salt or solvate thereof with one of more pharmaceutically acceptable carriers or excipients.

Compounds of formula (I) and physiologically acceptable salts and solvates thereof may be formulated for administration by any route, and the appropriate route will depend on the disease being treated. Suitable pharmaceutical formulations include those for oral, rectal, nasal, topical (including buccal and sublingal), vaginal or parenteral (including intramuscular, sub-cutaneous, intravenous, and directly into the affected tissue) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets, or tablets each containing a predetermined amount of the active ingredient; as a powder or granules; as a solution, a suspension or as an emulsion. The active ingredient may also be presented as a bolus, electuary, or paste. Tablets and capsules for oral administration may contain conventional excipients such as binding agents, fillers, lubricants, disintegrants, or wetting agents. The tablets may be coated according to methods known in the art. Timed release formulations which are known in the art may also be suitable. Oral liquid preparations may be in the form of, for example, aqueous or oily suspensions, solutions, emulsions, syrups, or elixirs, or may be presented as a dry product for constitution with water or other suitable vehicle before use. Such liquid preparations may contain conventional additives such as suspending agents, non-aqueous vehicles (which may include edible oils), or preservatives.

The compounds according to the invention may also be formulated for parenteral administration (e.g. by injection, for example bolus injection or continuous infusion) and may be presented in unit dose form in ampules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form, obtained by asceptic isolation of sterile solid or by lyophilization from solution, for constitution with a suitable vehicle, e.g. sterile, pryogen free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouth washes comprising the active ingredient in a suitable liquid carrier. For topical administration to the eye, the compounds according to the invention may be made up in a solution or suspension in a suitable sterile aqueous or non-aqueous vehicle. Additives such as buffers (e.g. sodium metabisulphite or disodium edeate) and thickening agents such as hypromellose may also be included.

Pharmaceutical formulations suitable for rectal administration wherein the carrier is a solid are possibly presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams, or sprays containing in addition to the active ingredient such as carriers as are known in the art to be appropriate.

For intra-nasal administration the compounds of the invention may be used as a liquid spray or dispersible powder or in the form of drops. Drops may be formulated with an aqueous or non-aqueous base also comprising one or more dispersing agents, solubilizing agents, or suspended agents. Liquid sprays are conveniently delivered form pressurized packs.

For administration by inhalation the compounds according to the invention are conveniently delivered from an insufflator, nebulizer or a pressurized pack or other convenient means of delivering the aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin of blister packs from which the powder may be administered with the aid of an inhaler or insufflator.

When desired the above described formulations adapted to give sustained release of the active ingredient may be employed.

The compounds and pharmaceutical compositions of the invention may also be used in combination with other therapeutic agents, for example antiinfective agents such as bactericidal or fungicidal agents, antiinflammatory agents or anticancer agents. In particular testosterone 5-reductase inhibitors or dopamine $D_2$ antagonists in combination with compounds and pharmaceutical compositions of the present invention may be used.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations. Appropriate doses of known therapeutic agents will be readily appreciated by those skilled in the art.

The amount of a compound of the invention required for use in treatment will of course vary not only with the particular compound selected but also with the route of administration, the nature of the condition being treated and the age and condition of the patient and will be ultimately at the discretion of the attendant physician. In general, however, a suitable dose will be in the range of form about 0.1 to 300 mg/kg of bodyweight per day, particularly from about 1 to about 100 mg/kg of bodyweight per day. An appropriate dosage unit involved in oral administration may generally contain from about 1 to 250 mg, particularly from about 25 to about 250 mg, of a compound of formula (I). The dosage employed for the topical administration will, of course, depend on the size of the area being treated. For they eyes each dose will by typically in the range of from 10 to 100 mg of the compound of the formula (I).

For use in treatment of -1C related disorders, in particular selective binding to the -1C receptor for treatment of benign prostatic hyperplasia, the compounds of the invention can be administered by any of the aforementioned routes, particularly by the oral route or by injection. The daily dosage for a 70 kg mammal will be in the range of about 5 mg to 5 g of a compound of formula (I).

EXAMPLES

The following examples illustrate aspects of this invention but should not be construed as limitations thereto.

Intermediate 1

5-(2-chloroethyl)-2-methoxy-benzenesulfonamide 1-(2-chloroethyl)-4-methoxy benzene (56.5 g, 331 mmol) is cooled to 0° C. and treated dropwise with chlorosulfonic acid (120 mL). The reaction is allowed to warm to 23° C. and stirred for 4 h. The purple mixture is poured cautiously and slowly into ice. This mixture is extracted with EtOAc (2×750 mL) and the combined organic layers are dried (MgSO$_4$) and concentrated to a brown oil. The oil is dissolved in THF (310 mL), cooled to −20° C., and a large excess of ammonia is condensed into the flask. The reaction is stirred for 1 h at 31 20° C., then allowed to warm to 23° C. and stirred for 15 h. The solvent is evaporated and the residue triturate with EtOAc. The off-white solid is washed with water and vacuum dried to afford the title compound as a white solid.

$^1$H NMR (DMSO-d6) d 7.62 (d, 1H, J=2.2 Hz), 7.47 (dd, 1H, J=8.6, 2.2 hz), 7.14 (d, 1H, J=8.5 Hz), 7.03 (s, 2H), 3.86 (s, 3H), 3.81 (t, 2H, J=6.9 Hz), 3.00 (t, 2H, J=6.8 Hz). C9h12NO3SCI requires C: 43.29 , H: 4.84, N: 5.61, found C: 43.27, H: 4.77, N: 5.59

Intermediate 2

4- (5-phenyl-oxazol-2-yl)-piperidine

A. 1-Acetyl-piperidine-4-carboxylic acid (2-oxo-2-phenyl-ethyl)-amide

A suspension of 1-acetyl-4-piperidine carboxylic acid (93 g, 542 mmol) in CH$_2$Cl$_2$ (700 mL) is treated portionwise at 23° C. with carbonyldiimidazole (80 g, 542 mmol). The solution is allowed to stir at 23° C. under N$_2$ for 1.5 h, then treated with 2-aminoacetophenone hydrochloride (93 g, 542 mmol) and diisopropylethylamine (113 mL, 650 mmol). The orange solution is stirred for 15 h, then washed with 2 N NaOH (2×200 mL), 2 N HCl (2×200 mL), and brine (1×300 mL), dried (MgSO) and concentrated to a red solid. The solid is dissolved in hot MeOH, and addition of hexane gave a pale orange solid which is obtained by filtration. The mother liquid is concentrated, the residue taken up in hot MeOH, and another crop of product is obtained by addition of hexane, to give a combined yield of 122 g of 1-Acetyl-piperidine-4-carboxylic acid (2-oxo-2-phenyl-ethyl)-amide as a pale orange solid.

$^1$H NMR (CDCl$_3$) d 7.97 (d, 2H, J=7.1 Hz), 7.63 (t, 1H, J=7.4 Hz), 7.50 (t, 2, J=7.9 Hz), 6.64 (br s, 1H), 4.76 (d, 2H, J=3.9 Hz), 4.62 (d, 1H, J=13.4 Hz), 3.88 (d, 1J=13.1 Hz), 3.12 (dt, 1H, J=12.2 Hz), 2.68 (dr, 1H, J=3.0 Hz), 2.48 (m, 1H), 2.10 (s, 3H), 1.92 (m, 2H), 1.74 (m, 2H).

C$_{16}$H$_{20}$N$_2$O$_3$ requires C: 66.65 H: 6.99, N: 9.72, found C: 66.79, H: 6.97, N: 9.69

B. 1-[4-(5-phenyl-oxazol-2-yl)-piperidine-1yl]-ethanone

A suspension of 1-acetyl-piperidine-4-carboxylic acid (2-oxo-2-phenyl-ethyl)-amide (1.1 g, 3.8 mmol), prepared as in Part A, in conc. H₂SO₄ (20 mL) is warmed to 65° C. for 1 h. The warm solution is poured into H₂O (250 mL), which is neutralized with solid NaHCO₃. This solution is extracted with EtOAc (2×200 mL) and the combined organic extracts are dried (MgSO₄) and concentrated to afford 1-[4-(5-phenyl-oxazol-2-yl)-piperidin-1-yl]-ethanone as a clear oil.
¹NMR (CDCl₃), d 7.59 (d, 2H, J=8.0 Hz), 7.40 (t, 2H, J=7.3 Hz), 7.30 (m, 1H), 7.22 (s, 1H), 4.49 (m, 1H), 3.87 (m, 1H), 3.24 (m, 1H), 3.11 (m, 1H), 2.92 (m, 1H), 2.11 (m, 5H), 1.88 (m, 2H).

C. 4-(5-phenyl-oxazol-2-yl)-piperidine

A solution of 1-[4-(5-phenyl-oxazol-2-yl)-piperidin-1-yl]-ethanone (30.0 g, 110.99 mmol), prepared as part B, in MeOH (450 ml) is treated with a solution of NaOH (44.40 g, 1109.90 mmol) in water (150 ml), heated at 75° C. for 18 hours, and then the reaction mixture is concentrated to ⅓ volume. Upon addition of ca. an equal volume of water, crystallization occurred. The solids are filtered, washed with water and dried in a vacuum over at 70° C. to afford 4-(5-phenyl-oxazol-2yl)-piperidine as a white solid.
¹HNMR (CDCl3): d 7.61 (d, 2H, J=7.4 Hz), 7.40 (t, 2H, J=7.4 Hz), 7.30 (t, 1H, J=7.4 Hz), 7.23 (s, 1H), 3.19 (d t, 2H, J=11.8, 3.3 hz), 2.99 (t t, 1H, J=11.8 3.9 Hz), 2.76 (m, 2H), 2.10 (m, 2H), 1.82 (m, 2H).
Mass spectrum: m/e calculated (MH+)=229.3, observed (MH+)=229.1.

Intermediate 3

1-[4-(4-Isobutoxymethyl-5-phenyl-oxazol-2-yl)-piperidin-1-yl]-ethanone

A. 1- Acetyl-piperidine-4-carboxylic acid (1-hydroxymethyl-2-oxo-2-phenyl-ethyl)-amide A solution of 1-Acetyl-piperidine-4-carboxylic acid (2-oxo-2-phenyl-ethyl)-amide (40.66 g, 141 mmol), prepared as in Intermediate 2A, in 2:1 EtOH: H₂O (160 mL EtOH, 80 mL H₂O) is treated with 37% aqueous formaldehyde (21.1 mL, 282 mmol) and NaCHO₃ (1.18 g, 14.1 mmol). The reaction mixture is stirred at 23° C. for 6 h, and the resulting precipitate is removed by filtration. The filtrate is cooled to 0° C. and diluted with H₂O (100 mL), and a second crop of 1-Acetyl-piperidine-4-carboxylic acid (1-hydroxymethyl-2-oxo-2-phenyl-ethyl)-amide is obtained by filtration.
¹h NMR (DMSO-d6), d 8.20 (d, 1H, J=7.6 Hz), 7.95 (d, 2H, J=7.5 Hz), 7.63 (m, 1H), 7.51 (m, 2H), 5.30 (m, 1H), 4.90 (t, 1H, J=5.6 Hz), 4.26 (m, 1H), 3.73 (m, 2H), 3.64 (m, 1H), 2.98 (m, 1H), 2.57 (m, 1H, partially observed by DMSO), 1.95 (s, 3H), 1.63 (m, 2H), 1.43 (m, 1H), 1.28 (m, 1H).
C17H22N2O4 requires C: 64.13, H: 6.97, N: 8.80, found C: 64.25, H: 7.03, N: 8.72

B. 1-[4-(4-chloromethyl-5-oxazol-2-yl)-piperidin-1-yl]-ethanone

1-Acetyl-peperidine-4-carboxylic acid (1-hydroxymethyl-2-oxo-2-phenyl-ethyl-)-amide (17 g, 85 mmol), prepared as in Part A, is dissolved in SOCl₂ (124 mL, 1.7 mole) and placed in a 78° C. oil bath for 15 min. The SOCl₂ is removed on a rotary evaporator, and the residue is partitioned between EtOAc (300 mL) and saturated aqueous NaHCO₃ (300 mL). The aqueous layer is extracted with EtOAc (2×100 mL), and the combined organic layers are dried (MgSO₄) and concentrated to a brown oil. The oil is purified by two chromatographies on silica (first column using EtOAc as eluent, second column using 10% EtOH: Hexane as eluent) to afford 1-[4-(4-chloromethyl-5-phenyl-oxazol-2-yl)-piperidin-1-yl]-ethanone as a yellow solid.
¹ NMR (CDCl₃) d 7.61 (m, 2H), 7.46 (t, 2H, J=7.3 Hz), 7.38 (m, 1H), 4.66 (s, 2H), 4.51 (m, 1H), 3.87 (m, 1), 3.08 (m, 1H), 2.87 (m, 1H), 2.10 (m, 5H), 1.86 (m, 2H).
C17H19N2O2Cl-0.5H2O requires C; 62.29, H: 6.15, N: 8.55, found C: 62.06, H: 6.16, N: 8.30

C. 1-[4-(4-Isobutoxymethyl-5-phenyl-oxazol-2-yl)-piperidin-1-yl]-ethanone

A solution of isobutyl alcohol (0.54 mL, 5.8 mmol) in THF (5 mL) is cooled to 0° C. and treated with sodium bis(trimethylsilyl)amide (5.8 mL of a 1 M solution in THF, 5.8 mmol) and stirred for 1 h. A solution of 1-[4-(4-chloromethyl-5-phenyl-oxazol-2-yl)-piperidin-1-yl]-ethanone (1.69 g, 5.3 mmol), prepared as in Part B, in THF (30 mL) is added dropwise, and the mixture is allowed to warm to 23° C., and stirred for 18 h. The reaction mixture is partitioned between EtOAc (150 mL) and H₂O (75 mL), and the organic layer is washed with brine (1×100 mL), dried (MgSO₄), and concentrated. The residue is purified by chromatography on silica using EtOAc as eluent to afford the title compound as a yellow oil.
¹H NMR (CDCl₃) d 7.69 (m, 2H), 7.46 (m, 2H), 7.37 (m, 1H), 4.53 (s, 2H), 3.90 (m, 1H), 3.37 (d, 2H, J=6.6 Hz), 3.25 (m, 1H), 3.11 (m, 1H), 2.90 (m, 1H), 2.14 (m, 6H), 1.94 (m, 3H), 0.95 (d, 6H, J=6.9 Hz).

Intermediate 4

4-(4-ethoxymethyl-5-phenyl-oxazol-2-yl)-piperidine

A solution of 1-[4-(4 -chloromethyl-5-phenyl-oxazol-2-yl)-piperidin-1-yl]-ethanone (0.200 g, 0.627 mmol), prepared as in intermediate 3B, in ethanol (4.5 ml) is treated with a solution of NaOH (0.501 g, 12.55 mmol) in water (1/.5 ml). The reaction mixture is heated to 75 C for 48 hours, concentrated, and the residue partitioned between EtOAc and water. The aqueous phase is washed with EtOAc (twice). The organic phases are combined and washed with saturated brine, dried (Na2SO4) and concentrated to afford the title compound as a light orange oil.
¹HNMR (CDCl₃): d 7.62 (m, 2H), 7.40 (, 2h), 7.30 (m, 1H), 4.50 (s, 2H), 3.62 (q, 2H, J=7.0 Hz), 3.13 (d t, 2H, J=12.6, 3.8 Hz), 2.92 (t t , 1H, J=11.4, 3.8 Hz), 2.70 (m, 2H), 2.05 (m, 2H), 1.78 (m, 2H), 1.24 (t, 3h, J=7.2 Hz).
Mass spectrum: m/e calculated (MH+)=2.874, observed (MH+)=287.1.

Intermediate 5

4-[5-phenyl-4-(2,2,2-trifluoro-ethoxymethyl)-oxazol-2-yl]-piperidine

A. 1-{4-[5-phenyl-4-(2,2,2-trifluoroethoxymethyl)-oxazol-2-yl]-piperidin-1-yl}-ethanone A solution of 1-[4-(4-chloromethyl-5-phenyl-oxazol-2-yl)-piperidin-1-yl]ethanone (30 g, 94.1 mmol), prepared as in Intermediate 3B, in 2,2,2-trifluoroethanol (450 ml) is treated with a solution of NaOH (56 g, 1412 mmol) in water (150 ml). After heating at 72° C. for 15 hours, the reaction mixture is concentrated. The residue is partitioned between EtOAc and water. The aqueous phase is reextracted once with EtOAc, and the combined organic phases are washed with saturated brine, dried (Na2SO4) and concentrated to afford 1-{4-[5-phenyl-4-(2,2,2-trifluoroethoxymethyl)-oxazol-2-yl]-piperidin-1-yl}-ethanone.

B. 4-[5-phenyl-4-(2,2,2-trifluoro-ethoxymethyl)-oxazol-2-yl]-piperidine

1-{4-[5-phenyl-4-(2,2,2-trifluoroethoxymethyl)-oxazol-2-yl]-piperidin-1-yl}-ethanone, prepared as in Part A, is redissolved in MeOH (450 ml) and treated with a solution of NaOH (56 g, 1412 mmol) in water (150 ml). After heating at 70 C for 20 hours, the reaction mixture is concentrated and the residue partitioned between EtOAc and water. The aqueous phase is reextracted six times with EtOAc, and the combined organic phases washed with saturated brine, dried (Na2SO4) and concentrated to a yellow oil which is purified by chromatography on silica using 10% MeOH: 89% $CH_2Cl_2$: 1% $NH_4OH$ to afford the title compound as a yellow solid.
$^1$HNMR ($CDCl_3$+MeOH-d4): d 7.56 (m, 2H), 7.34 (m, 3H), 4.63 (s, 2H), 3.90 (q, 2H, J=8.8 Hz), 3.09 (m, 2H), 2.92 (m, 1H), 2.66 (m, 2H), 2.04 (m, 2H), 1.74 (m, 2H).

Intermediate 6

2-[5-(2-Chloro-ethyl)-2-methoxy-benzenesulfonylamino]-acetamide 5-(2-chloro-ethyl)-2-methoxy-benzenesulfonyl chloride (5.78 g, 21.5 mmol) is dissolved in dioxane (72 mL). To this solution is added glycinamide hydrochloride (4.75 g, 42.9 mmol) and N,N-diisopropylethylamine (7 mL, 42.9 mmol) with stirring at room temperature for 24 h. The solution is diluted with ethyl acetate (100 mL) and washed with 1 M $H_3PO_4$ (2×50 mL), sat $NaHCO_3$, (1×50 mL,) brine (1×50 mL). The organic phase is dried with $Na_2SO_4$, filtered and the volatiles concentrated to a white solid. The solid is collected on a buchner by vacuum filtration and washed with ether to provide the title compound.
$R_f$=0.13 ethyl acetate in hexanes (3:1); $^1$H NMR (400 MHz, DMSO-$d_6$) d 7.60 (d, 1H, J=2.2 hz), 7.48 (dd, 1H, J=8.6, 2.2 Hz), 7.18–71.0 (m, 4H), 3.84 (s, 3H), 3.80 (t, 2H, J=6.8 Hz), 3.37 (d, 2H, J=4.2 Hz), 2.99, (t, 2H, J=6.8 Hz).

Intermediate 7

4-[4-Phenyl-3-(2-methyl-1-propyloxymethyl)oxazol-2-yl]piperidine

A solution of 4-[(4-phenyl-3-chloromethyl)oxazol-2-yl]-1-acetylpiperidine (33.0 g, 104 mmol) in 210 mL of isobutyl alcohol is treated at 25° C. with a solution of sodium hydroxide (41.4 g, 104 ) in 70 mL of water. The mixture is stirred at 105° C. for 24 h, at which time the mixture is allowed to cool to 25° C. and is concentrated in vacuo. The residue is taken up in water and is extracted with two 200-mL portions of ethyl acetate. The combined organic phases are washed with brine and are dried over magnesium sulfate. The crude product is chromatographed on silica gel (elution with dichloromethane followed by 20% methanol-dichloromethane) to provide the title compound as an oil.

$^1$H NMR ($CDCl_3$) d 7.67 (d, J=8 Hz, 2H), 7.42 (f, J=8 Hz, 2H), 7.34 (t, J=8 Hz, 1H), 4.51 (s, 2H), 3.34 (d, J=7 Hz, 2H), 3.17 (bd, J=13 Hz, 2H), 2.96 (m, 1H), 2.75 (t, 2H), 2.08 (bd, J=13 Hz, 2H), 1.95 (m, 1H), 190 (m, 3H), 0.91 (d, J=7 Hz, 6H) ppm.

Intermediate 8

4-[5-(4-fluoro-phenyl)-4-(2,2,2-trifluoro-ethoxymethyl)-oxazol-2-yl]-piperidine

A. 1-Acetyl-piperidine-4-carboxylic acid [2-(4-fluoro-phenyl)-2-oxo-ethyl]-amide To a 22-L flask is added 526.4 g (3.07 mol) of 1-acetylpiperidine-4-carboxylic acid, 8 L of methylene chloride, and 55 mL of DMF. To the resultant heterogeneous suspension is added 508.9 g (3.13 mol) of carbonyl diimidazole in two portions at room temperature. After two hours, 583.5 g (3.07 mol) of 2-Amino-1-(4-fluoro-phenyl)-ethanone hydrochloride (J. Heterocylcic Chem (1987), 24, 297. ) is added and the resultant mixture is allowed to stir overnight. The reaction mixture is extracted with 2 N HCl (3×1 L), saturated sodium bicarbonate solution (3×1 L), brine (1×1 L), dried over sodium sulfate, and filtered. To the filtrate is added toluene and the solution is concentrated in-vacuo to ca. 100 mL and the resultant precipitate is filtered. The solid is dried in-vacuo at 60° C. for 18 h to give 800 g of 1-Acetyl-piperidine-4-carboxylic acid[2-(4-fluoro-phenyl)-2-oxo-ethyl]-amide as an off-white solid.
$^1$HNMR (400 MHz, $CDCl_3$) d 7.97 (dd, J=9,3 Hz, 2H), 7.14 (t, J=32 9 Hz, 2H), 6.63 (br s, 1H), 4.69 (d, J=4 Hz, 2 H), 4.58 (d, 13 Hz, 1H), 3.85 (d, J=14 Hz, 1H), 3.09 (dt, J=13, 3 Hz, 1H), 2.65 (dr, 13, 3 Hz, 12H), 2.46 (tt, J=12, 4 Hz, 1H), 2.07 (s, 3H), 1.90 (m, 2H), 1.68 (m, 2H).

B. 1-Acetyl-piperidine-4-carboxylic acid [2-(4-fluoro-phenyl)-1-hydroxymethyl-2-oxo-ethyl]-amide To a 250 mL 3-neck flask under $n_2$ is added 8.00 g (26.1 mmol) of 1-Acetyl-piperidine-4-carboxylic acid [2-(4-fluoro-phenyl)-2-oxo-ethyl]amide, prepared as in Part A, to a 3:1 solution of EtOH:$H_2O$ (40 mL). While stirring the resultant solution at room temperature, 500 mg (5.95 mmol) of sodium bicarbonate is added followed by subsequent addition of 4.24 mL (52.23 mmol) of 37% formaldehyde over 5 min. The mixture is stirred for 1.5 h and then 20 mL of $H_2O$ is added. The reaction is cooled to –5° C. at which point a precipitate formed and is filtered. The mother liquor is again cooled to give a second crop of product and the combined lots are dried in-vacuo overnight at 65° C. to yield 1-Acetyl-piperidine-4-carboxylic acid [2-(4-fluoro-phenyl)-1-hydroxymethyl-2-oxo-ethyl]-amide as a white solid.
$^1$H NMR (400 MHz, $CDCl_3$) d 8.04 (m, 2H), 7.56 (d, 7.3 Hz, 1H), 7.16 (m, 2H), 5.55 (m, 1H), 4.62–4.45 (m, 2H), 3.84 (m, 3H), 3.17 (t, 13 Hz, 1H), 2.68 (t, 12.7 Hz, 1H), 2.48 (m, 1H), 2.08 (s, 3H), 1.91–1.65 (m, 4H).

C. 1-(4-[5-(4-fluoro-phenyl)-4-hydroxymethyl-oxazol-2-yl]-piperidin-1-yl)-ethanone To a slurry of 1-Acetyl-piperidine-4-carboxylic acid [2-(4-fluoro-phenyl)-1-hydroxymethyl-2-oxo-ethyl]-amide, prepared as in Part B, (100 g, 0.30 mol) and pyridine (100 mL, 1.20 mole) in dichloromethane (900 mL) at –40° C. is added trifluoroacetic anhydride (200 mL, 1.40 mole) over 1.5 hrs. The reaction is allowed to warm to −10° C. over 2 hrs and stirred at −10° C. for 1.5 hrs. Water (200 mL) is added, keeping the temperature at 0°—5° C. The layers are separated and the dichloromethane is washed with water (6×400 mL), dried (MgSO$_4$) and concentrated to a yellow oil. The oil is taken up in methanol (600 mL) and silica gel (100 g) is added and the mixture stirred at 20° C. for 16 hrs. The silica gel is removed by filtration, rinsed with methanol (400 mL) and the filtrate is concentrated. Ether (500 mL) is added to the residue and stirred for 2 hrs and the resulting solid is filtered to afford 1-(4-[5-(4-fluoro-phenyl)-4-hydroxymethyl-oxazol-2-yl]-piperidin-1-yl)-ethanone as a pale yellow solid.
$^1$H NMR (CDCl$_3$) d 1.75–2.00 (m, 2H), 2.00–2.25 (m, 2H), 2.15 (s, 3H), 2.80–3.35 (m, 4H), 3.85–3.95 (m, 1H), 4.52–4.62 (m, 1H), 1.75 (s, 2H), 7.13–7.23 (m, 2H), 7.60–7.70 (m, 2H).

D. 1-(4-[5-(4-fluoro-phenyl)-4-(2,2,2- trifluoro-ethoxymethyl)-oxazol-2-yl]-piperidin-1-yl)-ethanone To a stirred mixture of 18.85 g (59.2 mmol) 1-(4-[5-(4-fluoro-phenyl)-4-hydroxymethyl-oxazol-2-yl]-piperidin-1-yl)-ethanone, prepared as in Part C, and 11.5 g (66.0 mmol) methanesulfonic anhydride in 300 ml anhydrous tetrahydrofuran, 13.06 ml (75 mmol) N,N-diisopropylethylamine is added at 10° C. over 20 minutes. The mixture is allowed to warm to 20° C. and stirred for 90 minutes at 20° C. When the mesylate formation is complete as monitored by $^1$H-NMR, 15 g (100 mmol) of solid sodium Iodide is added. The conversion of the mesylate to the iodide is complete (as monitored by $^1$H-NMR) in about 2 hr. A solution of sodium 2,2,2-trifluoroethoxide, made from 21.8 ml (300 ml) 2,2,2-trifluoroethanol, 12 g (300 mmol) sodium hydride (60% disp. in mineral oil) in 280 ml anhydrous tetrahydrofuran, is added to reaction mixture. The resulting slurry is stirred at room temperature for 60 minutes, diluted with 500 mL ether, and extracted with water (3×200 mL). The water phase is extracted with methylene chloride (2×200 mL), and the organic phases are combined, dried with anhydrous magnesium sulfate, filtered, and concentrated under reduced pressure. The residue is then transferred to a silica gel packed column and purified using the following solvent mixtures: hexane-ethyl acetate (1:1), ethyl acetate (neat) then ethyl acetate-ethanol (9:1) to yield the title compound. $^1$H-NMR (CDCl$_3$) d 1.88 (m, 2H), 2.10–2.20 (m, 2H), 2.16 (d, 3H), 2.91 (t, 1H), 3.12 (m, 1H), 3.28 (t, 1H), 3.93 (d, 1H), 4.00 (q, 2H), 4.57 (d, 1H), 4.71 (s, 2H), 7.19 (t, 2H), 7.65 (dd, 2H).

E. 4-[5-(4-fluoro-phenyl)-4-(2,2,2-trifluoro-ethoxymethyl)-oxazol-2-yl]-piperidine A solution of 170 g (4.25 mol) sodium hydroxide in 250 mL of water is added to a stirred solution of 84 g (210 mmol) 1-(4-[5-(4-fluoro-phenyl)-4-(2,2,2-trifluoro-ethoxymethyl)-oxazol-2-yl]-piperidin-1-ethanone, prepared as in Part D, in 1L of methanol. The mixture is stirred at 50° C. for 8 hours, cooled to 20° C., and stirred for an additional 12 hrs. The methanol is removed from the reaction mixture under reduced pressure, and the residue is diluted with 1 L water. The mixture is extracted with methylene chloride (3×300 mL). The layers are separated and 50 g of sodium chloride mL). is added to the aqueous phase. The aqueous phase is extracted with methylene chloride (3×300 mL). The organic phases are combined, dried with anhydrous magnesium sulfate, filtered, then concentrated under reduced pressure. The residue is dissolved in 200 mL of ethyl acetate and 600 mL of saturated sodium bicarbonate solution is added and the mixture is stirred at room temperature for 12 hours. The solid is filtered and washed three times with 200 mL of water, and with ether (3×50 mL). The product is dried under reduced pressure at 40° C. to yield the title compound.
$^1$H-NMR (CDCl$_3$) d 0.79 dq (2H), 2.06 dd (2H), 2.73 dt (2H), 2.94 m (1H), 3.16 dt (2H), 3.95 q (2H), 4.67 s (2H), 7.13 t (2H), 7.61 dd (2H).

Intermediate 9

4-[5-(2,4-Difluoro-Phenyl)-4-(2,2,2-Trifluoro-Ethoxymethyl)-Oxazol-2-yl]-Piperidine, TFA salt A. 5-(2,4-Difluoro-phenyl)-oxazole-4-carboxylic acid methyl ester To a 500 ml three neck flask fitted with mechanical stirrer under nitrogen is added 2,4-difluorobenzoyl chloride (141 mmol, 25 g), methyl isocyanoacetate (143 mmol, 13 mL), triethylamine (424 mmol, 60 mL) and tetrahydrofuran (200 mL). The mixture is stirred for 72 hours at room temperature. The reaction is concentrated to a thick slurry and then transferred to a separatory funnel using 500 mls of distilled water. The aqueous mixture is extracted with ethyl acetate (4×250 mL). The ethyl acetate washes are combined and washed with brine. The organics are dried over anhydrous magnesium sulfate and concentrated in vacuo. The resulting residue is disolved in hot ethanol (400 mL) and treated with decolorizing carbon and magnesium sulfate. After 15 minutes, the mixture is filtered to remove the insolubles. To the filtrate is added to one liter of distilled water. A precipitate forms and the resultant mixture is allowed to stand. The resulting solid is collected by filtration and is washed with copious amounts of water. The resulting solid is dried under vacuum to give the title compound.
$^1$H NMR (300 MHz, CDCl$_3$) d 8.03 (s, 1H), 7.73 (m, 1H), 7.04 (m, 2H), 3.94 (s, 3H).

B. 2-Amino-3-(2,4-difluoro-phenyl)-3-oxo-propionic acid methyl ester, hydrochloride To a 1 liter three neck round bottom flash equipped with mechanical stirrer and reflux condensor is added 5-(2,4-Difluoro-phenyl)-oxazole-4-carboxylic acid methyl ester (30.66 g, 128 mmole), 200 mL of 2 normal hydrogen chloride in methanol, and 200 mL of dry methanol under nitrogen. The mixture is stirred and heated to 60° C. for three hours. The reaction is cooled and concentrated to a thick slurry. The slurry is treated with 100 mls of dry methanol and 400 mL of diethyl ether to precipitate solids. The solids are collected by vacum filtration and washed thoroughly with diethyl ether and air dried to yield the title compound.
$^1$H NMR (300 MHz, DMSO-d6) d 8.22 (m, 1H), 7.57 (m, 1H), 7.38 (m, 1H), 5.95 (s, 1H), 3.71 (s, 3H).

C. 4-[2-(2,4-Difluoro-phenyl)-1-methoxycarbonyl-2-oxo-ethylcarbamoyl]-piperidine-1-carboxylic acid benzyl ester To a three neck 1 liter round bottom flash fitted with mechanical stirrer, nitrogen inlet and dropping funnel are added n-carbobenzyloxy-isonipecotic acid (22.64 g, 86.2 mmol). 550 mL of dry tetrahydrofuran, and N-methyl morpholine, (19 mL, 712.4 mmol). The mixture is cooled to negative 20° C. and then isobutyl chloroformate (11.2 mls, 86.2 mmol in 90 mL of dry tetrahydrofuran) is added dropwise while maintaining the internal temperature at negative 20° C. After 1 hour at negative 20° C., the 2-Amino-3-(2,4-difluoro-phenyl)-3-oxo-propionic acid methyl ester, hydrochloride (22.89 g, 86.2 mmol) is added, followed by N-methyl morpholine, 9.5 mL. The reaction is allowed to come to room temperature is stirred for an additional 16 hours. The reaction is concentrated to a thick slurry and then extracted with dichloromethane, 350 mL, and water, 300 mL. The organic layer is washed with additional water. The aqueous layers are combined and washed with dichloromethane. The organic layers are combined and washed with brine and then dried with magnesium sulfate, filtered, and concentrated to give an oil. The oil is purified by preparative high performance liquid chromatography to give upon concentration of the desired fractions to yield the title compound.

$^1$H NMR (400 MHz, CDCl$_3$) d 7.91 (m, 1H), 7.30 (m, 4H), 6.95 (m, 2H), 6.87 (m, 1H), 6.05 (d, 1H, J=5.7 Hz), 5.08 (s, 2H), 4.15 (m, 2H), 3.66 (s, 3H), 2.83 (m, 2H), 2.41 (m, 1H), 1.80 (m, 2H), 1.66 (m, 2H).

D. 4-[5-(2,4-Difluoro-phenyl)-4-methoxycarbonyl-oxazol-2-yl]-piperidine-1-carboxylic acid benzyl ester To a 1 liter round bottom flask fitted with a condenser, nitrogen inlet, and magnetic stir bar is added 4-[2-(2,4-Difluoro-phenyl)-1-methoxycarbonyl-2-oxo-ethylcarbamoyl]-piperidine-1-carboxylic acid benzyl ester, (32 g, 67.4 mmol), and 120 mL of thionyl chloride. The mixture is immersed in an oil bath preheated to 70° C. and stirred for 10 minutes. The reaction is removed, cooled to room temperature and concentrated to an amber oil. The amber oil is carefully treated with about 50 g of ice, and 350 mL of saturated sodium bicarbonate. The resulting mixture is extracted with 3×100 mL of diethyl ether. The organic layers are combined, washed with brine, dried over magnesium sulfate and concentrated to a thick amber paste to yield the title compound.

$^1$H NMR (300 MHz, CDCl$_3$) d 7.68 (m, 1H), 7.36 (m, 5H), 6.98 (m, 2H), 5.15 (s, 2H), 4.22 (m, 2H), 3.87 (s, 3H), 3.06 (m, 3H), 2.10 (m, 2H), 1.91 (m, 2H).

E. 4-[5-(2,4-Difluoro-phenyl)-4-hydroxymethyl-oxazol-2-yl]-piperidine-1-carboxylic acid benzyl ester To a 0.5 liter round bottom flask fitted with a condenser, nitrogen inlet, and mechanical stirrer is added 30.25 g, 66.3 mmoles of 4-[5-(2,4-Difluoro-phenyl)-4-methoxycarbonyl-oxazol-2-yl]-piperidine-1-carboxylic acid benzyl ester, and a mixture of methanol and ether (4 mL to 200 mL). Lithium borohydride 2.17 g (0.1 mol) is added in three portions and then the mixture is stirred and heated to reflux for 30 minutes. The reaction is allowed to cool and carefully quenched with 400 mL of 0.5 N hydrochloric acid. The resulting mixture is extracted with 3×200 mL of methylene chloride. The organics are combined, washed with brine, dried over magnesium sulfate and concentrated to a thick residue to yield the title compound.

$^1$H NMR (300 MHz, CDCl$_3$) d 7.55 (m, 1H), 7.39 (m, 5H), 7.02 (m, 2H), 5.17 (s, 2H), 4.65 (s, 2H), 4.22 (m, 2H), 3.35 (br, 1H), 3.07 (m, 3H), 2.10 (m, 2H), 1.89 (m, 2H).

F. 4-[5-(2,4-Difluoro-phenyl)-4-(2,2,2-trifluoro-ethoxymethyl)-oxazol-2-yl]-piperidine-1-carboxylic acid benzyl ester To a three neck 0.5 liter round bottom flask fitted with mechanical stirrer, nitrogen inlet and dropping funnel is added 4-[5-(2,4-Difluoro-phenyl)-4-hydroxymethyl-oxazol-2-yl]-piperidine-1-carboxylic acid benzyl ester, methane sulfonic anhydride (5.87 g, 33.7 mmol), and 150 mL of dry tetrahydrofuran. The mixture is stirred and cooled to 0° C., followed by dropwise addition of diisopropyl ethylamine (8.4 mL, 48 mmol). The mixture is stirred for 1 hour at 0° C. and then allowed to warm to room temperature. To the resultant mixture is then added sodium iodide (7.75 g, 51.7 mmol), and the mixture is stirred for an additional three hours. The sodium 2,2,2-trifluoroethoxide (0.151 mmol in 80 mL of dry tetrahydrofuran) is added dropwise over a 15 minute period and the resulting mixture is stirred for an additional 1 hour. The mixture is cooled to 0° C. and carefully quenched with 125 mL of water. After the addition was complete, the mixture is extracted with water and methylene chloride. The aqueous is washed with an additional three portions of methylene chloride, using 300 mL volumes. The organics are combined, washed with brine, dried over magnesium sulfate and concentrated to a thick residue. The residue is purified by preparative medium performance liquid chromatography to give upon concentration the desired fractions of the title compound.

$^1$H NMR (300 MHz, CDCl$_3$) d 7.56 (m, 1H), 7.40 (m, 5H), 7.02 (m, 2H), 5.18 (s, 2H), 4.65 (s, 2H), 4.22 (m, 2H), 3.98 (q, 2H, J=8.8 Hz), 3.08 (m, 3H), 2.11 (m, 2H), 1.91 (m, 2H).

G. 4-[5-(2,4-Difluoro-phenyl)-4-(2,2,2-trifluoro-ethoxymethyl)-oxazol-2-yl]-piperidine, TFA salt To a 200 ml flask is added 4-[5-(2,4-Difluoro-phenyl)-4-(2,2,2-trifluoro-ethoxymethyl)-oxazol-2-yl]-piperidine-1-carboxylic acid benzyl ester, (11.4 g, 22.3 mmol), and a stir bar. The flask is cooled to 0° C., followed by the addition of 55 mL of trifluoroacetic acid. The mixture is stirred under nitrogen and allowed to slowly come to room temperature and stir for 72 hours. The reaction is concentrated to a thick oil, and co-evaporated with toluene three times using 100 mL portions of toluene. To the resultant material is added 100 mL of diethyl ether and the mixture is stirred for 16 hours. The resultant solid is collected by filtration to give after drying the title compound as white solids.

$^1$H NMR (300 MHz, DMSO-d6) d 9.03 (br, 1H), 8.75 (br, 1H), 7.67 (m, 1H), 7.50 (m, 1H), 7.30 (m, 1H), 4.60 (s, 2H), 4.14 (q, 2H, J=9.5 Hz), 3.35 (m, 3H), 3.09 (m, 2H), 2.21 (m, 2H), 1.96 (m, 2H).

Intermediate 10

4-(2-{4-[5-(4-Fluoro-Phenyl)-4-(2,2,2-Trifluoro-Ethoxymethyl)-Oxazol-2-yl]-Piperidin-1-yl}-Ethyl)-Benzoic Acid Methyl Ester A. 4-(2-Chloro-ethyl)-benzoic acid methyl ester A solution of 4-(2-Chloro-ethyl)-benzoic acid (20 g, 108 mmol) in DMF (200 mL) is treated with K$_2$CO$_3$ (59.7 g, 432 mmol) and MeI (16.8 mL, 270 mmol) and stirred at 23 C for 18 h. The reaction mixture is diluted with EtOAc (450 mL) and washed with H$_2$O (2×150 mL), saturated aqueous NaHCO$_3$ (1×200 mL), brine (1×200 mL), dried (MgSO$_4$), and concentrated to afford the title compound as a yellow oil.

$^1$H NMR (400 MHz, CDCl$_3$) d 7.97 (d, 2H, J=8.2 Hz), 7.27 (d, 2H, J=8.2 Hz), 3.89 (s, 3H), 3.72 (t, 2H, J=7.2 Hz), 3.10 (t, 2H, J=7.2 Hz).

B. 4-(2-{4-[5-(4-Fluoro-phenyl)-4-(2,2,2-trifluoro-ethoxymethyl)-oxazol-2-yl]-piperidin-2-yl}-ethyl)-benzoic acid methyl ester A solution of 4-[5-(4-Fluoro-phenyl)-4-(2,2,2-trifluoro-ethoxymethyl)-oxazol-2-yl]-piperidine (27.1 g, 57.3 mmol), prepared as in Intermediate 8, 4-(2-Chloro-ethyl)- acid methyl ester (14.8 g, 74.5 mmol), prepared as in part A, diisopropyl ethyl amine (31.4 mL, 180 mmol), and Li Br (6.5 g, 74.5 mmol) in dioxane (100 mL) is heated at 105 C. for 18 h. The reaction mixture is diluted with EtOAc (300 mL) and washed with $H_2O$ (1×100 mL), brine (1×150 mL), dried ($Na_2SO_4$), and concentrated to an oil. The oil is purified by chromatography on silica using 20:80 Hexane:EtOAc as eluent to afford the title compound as white solids.
$^1$H NMR (400 MHz, $CDCl_3$) d 7.93 (d, 2H, J=8.2 Hz), 7.61 (m, 2H), 7.26 (d, 2H, J=8.2 Hz), 7.13 (m, 2H), 4.67 (s, 2H) 3.95 (q, 2H, J=8.7 Hz), 3.88 (s, 3H), 3.03 (m, 2H), 2.84 (m, 3H), 2.64 (m, 2H), 2.07–2.20 (m, 4H), 1.97 (m, 2H). $C_{27}H_{28}N_2O_4F_4$ required C:62.3, H:5.42, N:5.38, found C:62.29, H:5.44, N:5.35.

Intermediate 11

4-(2-{4-[5-(4-Fluoro-Phenyl)-4-(2,2,2-Trifluoro-Ethoxymethyl)-Oxazol-2-yl]-Piperidin-1-yl}-Ethyl)-Benzyl Amine A. 4-(2-{4-[5-(4-Fluorophenyl)-4-(2,2,2-trifluoro-ethoxymethyl)-oxazol-2-yl]-piperidin-1-yl}-ethyl)-phenyl)-methanol A suspension of LAH (607 mg, 16 mmol) in THF (20 mL) is treated dropwise with a solution of 4-(2-{4-[5-(4-Fluoro-phenyl)-4-(2,2,2-trifluoro-ethoxymethyl)-oxazol-2-yl]-piperidin-2-yl}-ethyl)-benzoic acid methyl ester (5.21 g, 10 mmol), prepared as in intermediate 10, and allowed to stir at 23 C. for 2 h. The reaction mixture is quenched by the sequential addition to $H_2O$ (0.6 mL dropwise), 15% NaOH (0.6 mL), and $H_2O$ (1.83 mL). The resultant slurry is filtered through celite, and the solvent evaporated. The residue is taken up in EtOAc (180 mL) and washed with saturated aqueous $NaHCO_3$ (1×100 mL), brine (1×100 mL), dried ($Na_2SO_4$), and concentrated to an oil that solidifies upon standing.
$^1$H NMR (400 MHz, $CDCl_3$) d 7.61 (m, 2H), 7.28 (m, 2H), 7.19 (m, 2H), 7.13 (m, 2H), 4.67 (s, 2H), 4.65 (s, 2H) 3.95 (q, 2H, J=8.7 Hz), 3.05 (m, 2H), 2.82 (m, 3H), 2.62 (m, 2H), 2.18 (m, 2H), 2.09 (m, 2H), 1.98 (m, 2H).

B. 4-(2-{4-[5-(4-Fluoro-phenyl)-4-(2,2,2-trifluoro-ethoxymethyl)-oxazol-2-yl]-piperidin-1-yl}-ethyl)-benzyl azide A solution of 4-(2-{4-[5-(4-Fluorophenyl)-4-(2,2,2-trifloro-ethoxymethyl)-oxazol-2-yl]-piperidin-1-yl}-ethyl)-phenyl]-methanol (970 mg, 2 mmol), prepared as in part A, and $Et_3N$ (0.3 mL) in $CH_2Cl_2$ (10 mL) is treated with methanesulfonyl chloride (0.17 mL, 2.2 mmol), and allowed to stir for 45 min. The solvent is evaporated and the residue taken up in DMF (12 mL), treated with $NaN_3$ (260 mg, 4 mmol), and allowed to stir at 50 C. for 2 h. The reaction mixture is diluted with EtOAc (150 mL), washed with saturated aqueous $NaHCO_3$ (1×100 mL), brine (1×100 mL), dried ($Na_2SO_4$), and concentrated to a yellow oil. The oil is purified by chromatography on silica using 2% MeOH:$CHCl_3$ as eluent to afford the title compound as a clear oil.

A small portion is converted to the HCl salt by treatment with 4 N HCl in dioxane, and then evaporation of the solvent.
$^1$H NMR (400 MHz, DMSO-d6) d 10.61 (br, 1H), 7.66 (m, 2H), 7.32 (m, 6H), 4.66 (s, 2H), 4.40 (s, 2H) 4.17 (q, 2H, J=9.4 Hz), 3.63 (m, 1.6H), 3.42 (m, 0.4H), 3.31 (m, 4H), 3.18 (m, 1H), 3.08 (m, 2H), 2.29 (m, 2H), 2.08 (m, 2H). $C_{26}H_{27}N_5O_2F_4$ required C:56.37, H:5.09, N:12.64, found C:56.33, H:5.08, N:12.58

C. 4-(2-{4-[5-(4-Fluoro-phenyl)-4-(2,2,2-trifluoro-ethoxymethyl)-oxazol-2-yl]-piperidin-1-yl}-ethyl)-benzyl amine A solution of 4-(2-{4-[5-(4-Fluoro-phenyl)-4-(2,2,2-trifluoro-ethoxymethyl)-oxazol-2-yl]-piperidin-1-yl}-ethyl)-benzyl azide (2.25 g, 4.3 mmol), prepared as in Part B, in EtOH (80 mL) is treated with 10% Pd/C (400 mg) and hydrogenated at 50 psi for 12 h. The catalyst is removed by filtration through celite, and the solvent evaporated to afford the title compound as off-white solids, which is used in subsequent reactions without purification.
Electrospray Mass Spec: $MH^+$=492.2

Intermediate 12

4-[5-(4-Chlorophenyl)-4-(2,2,2-Trifluoroethoxymethyl)-Oxazol-2-yl]-Piperidine Trifluoroacetate A. 2-Amino-4'-chloroacetophenone hydrochloride To a stirred solution of 2-bromo-4'-chloroacetophenone (10.34 g, 43.40 mmol) and 18-crown-6 (1.16 g, 4.34 mmol) in acetonitrile (150 mL) at room temperature (RT) is added sodium diformylamide (12.51 g, 131.6 mmol). After 3 h at RT and 2 h at 40° C., the suspension is diluted with water (100 mL) and extracted with ethyl acetate (4×150 mL). The combined organics are washed with brine, dried (magnesium sulfate), and concentrated to afford waxy yellow solids. These are taken up in absolute ethanol (150 mL), the stirred solution is treated with concentrated hydrochloric acid (15.00 mL, 174 mmol), and the mixture is heated to reflux for 1.5 h. The suspension is cooled to RT, filtered, and the solids are washed with ethyl acetate. Drying in vacuo at RT afforded the title compound as white solids.
mp=262–265° C. (dec.) $^1$H NMR (400 MHz, $CD_3OD$) d 4.67 (s, 2H), 7.63 (d, 2H, J=8.6 Hz), 8.05 (d, 2H, J=8.6 Hz).

B. 4-[2-(4-Chlorophenyl)-2-oxo-ethylcarbamoyl]-piperidine-1-carboxylic acid benzyl ester To a stirred solution of N-carbobenzoxy-isonipecotic acid (10.49 g, 39.84 mmol) and 4-methylmorpholine (NMM) (500 mL, 45.0 mmol) in anhydrous dichloromethane (200 mL) under $N_2$ and cooled in an −25° C. bath is added isobutyl chloroformate (5.30 mL, 40.0 mmol) dropwise. Following complete addition, the suspension is stirred for 5 min, then 2-amino-4'-chloroacetophenone hydrochloride (7.4632 g, 36.217 mmol), prepared as in Part A, is added, followed by NMM (10.10 mL, 90.94 mmol). After stirring in the −25° C. bath for 30 min, the suspension is allowed to warm to RT over 1.5 h. To the solid reaction mixture is added half-saturated aqueous sodium bisulfate, dichloromethane, and ethyl acetate. The solids are collected, washed with dichloromethane, and heated to reflux in THF (300 mL) for 30 min. The mixture is filtered and the filtrate concentrated to about 1/20th volume. Diethyl ether is added, the precipitated solids are collected, and dried in vacuo at RT to afford the product as fluffy, white solids.

$^1$H NMR (400 MHz, DMSO-$d_6$) d 1.41 (m, 2H), 1.70 (m, 2H), 2.42 (m, 1H), 2.82 (br, m, 2H), 4.00 (d, 2H) 4.58 (d, 2H), 5.05 (s, 2H), 7.38 (m, 5H), 7.60 (d, 2H), 7.98 (d, 2H), 8.22 (m, 1H).

C. 4-[-2-(4-Chlorophenyl)-1-hydroxymethyl-2-oxo-ethylcarbamoyl]-piperidine-1-carboxylic acid benzyl ester To a stirred solution of the 4-[2-(4-chlorophenyl)-2-oxo-ethylcarbamoyl]-piperidine-1-carboxylic acid benzyl ester (8.91 g, 21.5 mmol), prepared as in Part B, and sodium bicarbonate (0.19 g, 2.3 mmol) in a mixture of water (10 mL) and dimethyl sulfoxide (50 mL) in a 50° C. water bath is added aqueous formaldehyde (3.30 mL, 44.0 mmol). After 6 h, the mixture is diluted with water (1 L) and allowed to stand overnight at RT. Filtration gives gummy solids which are triturated with ethyl acetate to give the desired product as white solids.

mp=116–118° C. $^1$H NMR (400 MHz, DMSO-$d_6$) d 1.40 (m, 2H), 1.62 (m, 2H), 2.21 (m, 1H), 2.80 (br s, 2H), 3.70 (m, 2H), 3.98 (m, 2H), 4.95 (br t, 1H), 5.02 (s, 2H), 5.23 (br q, 1H), 7.38 (m, 5H), 7.60 (d, 2H), 7.98 (d, 2H), 8.25 (d, 1H).

D. 4-[5-(4-Chlorophenyl)-4-hydroxymethyl-oxazol-2-yl]-piperidine-1-carboxylic acid benzyl ester To a stirred solution of 4-[-2-(4-chlorophenyl)-1-hydroxymethyl-2-oxo-ethylcarbamoyl]-piperidine-1-carboxylic acid benzyl ester 5.61 g, 12.6 mmol), prepared as in Part C, imidazole (1.75 g, 25.4 mmol), and 4-dimethylaminopyridine (0.0770 g, 0.62 mmol) in dry N,N-dimethylformamide (50 mL) at RT under $N_2$ is added t-butyldimethylsilyl chloride (2.94 g, 18.9 mmol). After 16 h, the mixture is diluted with water, acidified to pH 3 with 1 N phosphoric acid, and extracted with diethyl ether (4×100 mL). The combined organics are washed with water (2×100 mL), with saturated aqueous sodium bicarbonate, and with brine. Drying (sodium sulfate) and concentration gave the silyl ether as a colorless glass which is used directly in the next step.

To a stirred solution of the silyl ether and pyridine (4.20 mL, 51.4 mmol) in anhydrous dichloromethane under $N_2$ with cooling in an ice water bath is added trifluoroacetic anhydride (3.60 mL, 25.2 mmol). After 30 min at ice bath temperature and 2 h at RT, the mixture is diluted with water (50 mL) and acidified to pH 2 with saturated aqueous sodium bisulfate. The mixture is extracted with dichloromethane (4×100 mL) and the combined organics are washed with water, saturated aqueous sodium bicarbonate, and with brine. Drying (magnesium sulfate) and concentration gives the oxazole silyl ether as a slightly yellow oil which is used directly in the next step.

A solution of the oxazole silyl ether and concentrated hydrochloric acid (10 drops) in methanol (30 mL) is stirred at RT for 1.5 d. The mixture is diluted with saturated aqueous sodium bicarbonate (5 mL) and concentrated. The residue is diluted with saturated aqueous sodium bicarbonate and extracted with dichloromethane (3×100 mL). The combined organics are dried (magnesium sulfate) and concentrated to an oil which is purified by flash chromatography (silica gel, ethyl acetate) to give the title compound as a colorless foam.

mp=97–99° C. $^1$H NMR (400 MHz, CDCl$_3$) d 1.80 (m, 2H), 2.03 (m, 2H), 3.00 (m, 3H), 4.10 (m, 1H), 4.20 (br s, 2H), 4.70 (d, 2H, J=5.4 Hz), 5.17 (s, 2H), 7.27–7.45 (m, 7H), 7.59 (d, 2H, J=1.7 Hz)).

Anal. Calcd for $C_{23}H_{23}ClN_2O_4$ (426.90 g/mol): C, 64.71; H, 5.43; N, 6.56. Found: C, 64.61; H, 5.38; N, 6.50.

E. 4-[5-(4-Chlorophenyl)-4-(2,2,2-trifluoroethoxymethyl)-oxazol-2-yl]-piperidine-1-carboxylic acid benzyl ester To a stirred solution of 4-[5-(4-chlorophenyl)-4-hydroxymethyl-oxazol-2-yl]-piperidine-1-carboxylic acid benzyl ester (3.9000 g, 9.1356 mmol), prepared as in Part D, and triethylamine (1.44 mL, 10.2 mmol) in anhydrous dichloromethane (30 mL) under $N_2$ is added methanesulfonyl chloride (0.79 mL, 10 mmol) dropwise with cooling in an ice water bath. After 15 min, the mixture is diluted with water, acidified to pH 2 with saturated aqueous sodium bisulfate, and extracted with dichloromethane (3×100 mL). The combined organics are washed with water, with saturated aqueous sodium bicarbonate, and dried over magnesium sulfate. Concentration gave the mesylate as a slightly yellow oil which is used directly in the next step.

To a stirred solution of the mesylate, sodium iodide (2.7749 g, 18.328 mmol), and tetrabutylammonium iodide (0.3479 g, 0.9230 mmol) in anhydrous tetrahydrofuran (20 mL) is added a solution of sodium 2,2,2-trifluoroethoxide in tetrahydrofuran (60 mL) [prepared at RT from 2,2,2-trifluoroethanol (2.20 mL, 29.9 mmol) and sodium hydride (1.0951 g, 60%, 27.38 mmol)]. After 2.5 d at RT, the suspension is diluted with water and extracted with ethyl acetate (3×100 mL). The combined organics are washed with water, with saturated aqueous sodium bicarbonate, with brine, and are dried over magnesium sulfate. Concentration and flash chromatography (silica gel, 33% ethyl acetate in hexanes) gave the title compound as a yellow oil.

$^1$H NMR (400 MHz, CDCl$_3$) d 1.85 (m, 2H), 2.12 (m, 2H), 3.02 (m, 3H), 3.96 (q, 2H, J=8.7 Hz), 4.20 (br s, 2H), 4.69 (s, 2H), 5.18 (s, 2H), 7.28–7.40 (m, 5H), 7.42 (d, 2H, J=8.5 Hz), 7.60 (d, 2H, J=8.5 Hz).

F. 4-[5-(4-Chlorophenyl)-4-(2,2,2-trifluoroethoxymethyl)-oxazol-2-yl]piperidine trifluoroacetate A solution of 4-[5-(4-Chlorophenyl)-4-(2,2,2-trifluoroethoxymethyl)-oxazol-2-yl]-piperidine-1-carboxylic acid benzyl ester (3.7600 g, 7.3880 mmol) in trifluoroacetic acid (10 mL, 130 mmol) was stirred at RT for 3 d, then concentrated to a thick oil. This is dissolved with heating in a mixture of hexane and diethyl ether which, upon cooling, precipitated cream-colored solids. These are collected, washed with hexane and dried in vacuo at RT. Reworking the mother liquors gives a second crop of solids. The crops are combined to give the title compound as cream colored solids.

mp=172–175° C. $^1$H NMR (400 MHz, CD$_3$OD) d 2.10 (m, 2H), 2.39 (m, 2H), 3.20 (m, 2H), 3.30 (m, 1H), 3.50 (m, 2H), 4.06 (q, 2H), 4.72 (s, 2H), 7.51 (d, 2H), 7.67 (d, 2H).

Intermediate 13

5-(2-Chloroethyl)-2-Methoxy-Benzenesulfonamide 1-(2-chloroethyl)-4-methoxy benzene (56.5 g, 331 mmol) is cooled to 0° C. and treated dropwise with chlorosulfonic acid (120 mL). The reaction is allowed to warm to 23° C.

and stirred for 4 h. The purple mixture is poured cautiously and slowly onto ice. This mixture is extracted with EtOAc (2×750 mL) and the combined organic layers are dried (MgSO$_4$) and concentrated to a brown oil. The oil is dissolved in THF (310 mL), cooled to −20° C., and a large excess of ammonia is condensed into the flask. The reaction is stirred for 1 h at −20° C., then allowed to warm to 23° C. and stirred for 15 h. The solvent is evaporated and the residue triturated with EtOAc. The off-white solid is washed with water and vacuum dried to afford the title compound as a white solid.
$^1$H NMR (DMSO-d6) d 7.62 (d, 1H, J=2.2 Hz), 7.47 (dd, 1H, J=8.6, 2.2 Hz), 7.14 (d, 1H, J=8.5 Hz), 7.03 (s, 2H), 3.86 (s, 3H), 3.81 (t, 2H, J=6.9 Hz), 3.00 (t, 2H, J=6.8 Hz). C9H12NO3SCI requires C: 43.29, H: 4.84, N: 5.61, found C: 43.27, H: 4.77, N: 5.59

Intermediate 14

2'-Diformylamino-4-Fluoroacetophenone

In a 2 l round bottomed flask combine 2'-chloro-4-fluoroacetophenone (189.2 g, 1.09 mmoles), acetonitrile (950 ml), sodium iodide (18.20 g, 0.110 moles) and sodium diformylamide (109.4 g, 1.15 moles), then heat to ethyl acetate: heptane (500 ml) and the filtrate concentrated to approximately 500 ml by distillation. After crystallization is complete, the product is collected by vacuum filtration, washed twice with 2:1 ethyl acetate: heptane (300 ml) and dried under vacuum for two hours to give 2'-diformylamino-4-fluoroacetophenone (190.3 g, 0.910 moles). $^1$H NMR (400 MHz, d6 DMSO) d 5.08 (s, 2H), 7.4 (t, 2H), 8.15 (q, 2H), 9.2 (s, 1H).

Intermediate 15

2'-Amino-4-Fluoroacetophenone Hydrochloride

In a 12 l round bottomed flask under N$_{2(g)}$ combine 2'-diformylamino-4-fluoroacetophenone (1.82 kg, 8.72 moles), absolute ethanol (7.5 l) and 12 M hydrochloric acid (2.5 l). The suspension is heated to reflux for six hours, then the reaction is cooled to ambient temperature and the product collected by vacuum filtration. The crystals are washed twice with cold absolute ethanol (500 ml each) and dried at ambient temperature under 27 in Hg vacuum to give 2'-amino-4-fluoroacetophenone hydrochloride (1.48 kg, 7.80 moles). $^1$H NMR (400 MHz, d6 DMSO) d 4.57 (s, 2H), 7.43 (t, 2H), 8.12 (q, 2H), 8.57 (bs, 3H).

Intermediate 16

1-Cyanomethyl-Piperidine-4-Carboxylic Acid-[2-(4-Fluorophenyl)-2-Oxoethyl]Amide

In a 22-l round bottomed flask, combine N-cyanomethyl isonopecotic Acid as a 1:1 mixture with sodium chloride (1.76 kg, 7.42 moles) and methylene chloride (8.0 l). To the suspension is added carbonyl diimidazole (1.20 kg, 7.42 moles) portionwise over thirty minutes. After stirring for one hour, 2'-amino-4-fluoroacetophenone hydrochloride (1.45 kg, 7.64 moles) is added and the suspension stirred for three hours. Methylene chloride (4.0 l) is removed by distillation, heptane (4.0 l) is added and the suspension stirred overnight. The crude product is collected by vacuum filtration, then resuspended in process water (3.0 l), slurried and re-collected. The aqueous wash is repeated twice, then the crystals are dried at ambient temperature under 25 in Hg vacuum to give 1-cyanomethyl-piperidine-4-carboxylic acid-[2-(4-fluorophenyl)-2-oxoethyl] amide (2.00 kg, 6.60 moles). $^1$H NMR (400 MHz, d6 DMSO) d 1.58 (m, 2H), 1.75 (m, 2H), 2.15 (m, 2H), 2.20 (m, 1H), 2.70 (d, 2H), 3.70 (s, 2H), 4.57 (d, 2H), 7.37 (t, 2H), 8.07 (q, 2H), 8.20 (t, 1H).

Intermediate 17

1-Cyanomethyl-Piperidine-4-Carboxylic Acid-[2-(4-Fluorophenyl)-1-Hydroxymethyl-2-Oxoethyl] Amide In a 22-l round bottomed flask, suspend 1-cyanomethyl-piperidine-4-carboxylic acid-[2-(4-fluorophenyl)-2-oxoethyl] amide (1.004 kg, 3.31 moles) in absolute ethanol (5.0 l) and process water (2.5 l). To the suspension is added sodium bicarbonate (55.62 g, 0.662 moles) and 37% formaldehyde (400 ml, 4.93 moles), then the suspension is warmed to 40° C. and the reaction followed by HPLC. Upon completion, the reaction is quenched by added ice water (5.0 l) and brine (5.0 l). The reaction is stirred for three hours, then the crystals are collected by vacuum filtration, washed with process water (1.0 l) and dried at ambient temperature and 25 in Hg to give 1-cyanomethyl-piperidine-4-carboxylic acid-[2-(4-fluorophenyl)-1-hydroxymethyl-2-oxoethyl] amide (839 g, 2.52 moles). $^1$H NMR (400 MHz, d6 DMSO) d 1.52 (m, 2H), 1.67 (t, 2H), 2.12 (t, 2H), 2.23 (m, 1H), 2.77 (m, 2H), 3.38 (s, 1H), 3.65 (m, 1H), 3.68 (s, 2H), 3.75 (m, 1H), 5.15 (m, 1H), 5.25 (m, 1H), 7.16 (t, 2H), 8.06 (q, 2H), 8.40 (d, 1H).

Intermediate 18

{4-[5-(4-Fluorophenyl)-4-Hydroxymethyl-Oxazol-2-yl]-Piperidin-1-yl} Acetonitrile In a 5-l round bottom flask combine 1-cyanomethyl-piperidine-4-carboxylic acid-[2-(4-fluorophenyl)-1-hydroxymethyl-2-oxoethyl] amide (100 g, 0.296 mole) and acetonitrile (1.4 l) and cool to −15° C. To the solution is added trifluoroacetic acid (22.8 mL, 0.296 mole) at such a rate as to maintain a temperature below −10° C. The resulting suspension is stirred at −10° C. to −15° C. for 10 minutes, then trifluoroacetic anhydride (125.6 mL, 0.890 mole) is charged at such a rate as to maintain a temperature below −10° C. After the addition is complete, a solution of pyridine (96.0 mL, 1.19 mole) in acetonitrile (50 mL) is added over 30 minutes maintaining a temperature of −15° C. The reaction mixture is warmed to room temperature, water (100 mL) is added then the reaction temperature is increased to 40° C. and the solution is stirred for 1.5 hours. The reaction mixture is concentrated to about 250 mL and a 1:1 mixture of saturated aqueous sodium chloride:water (1.5 l) is added. The aqueous suspension is washed with ethyl acetate (4×800 mL) and to the combined organic extracts is added sodium sulfate (100 g) and Dacro brand activated carbon (100 g). After sitting 1 hour, the slurry is filtered through sintered glass and concentrated to an oil. The oil is dissolved in acetonitrile (200 mL) and saturated aqueous sodium bicarbonate (1.2 l) is added in portions to effect crystallization of the free base. The resulting slurry is cooled to 0° C., the solids are collected by filtration and dried to constant weight to give {4-[5-(4-fluorophenyl)-4-hydroxymethyl-oxazol-2-yl]-piperidin-1-yl} acetonitrile (85 g, 0.255 mole) as a monohydrate $^1$H NMR (400 MHz, CDCl$_3$) d 1.91 (m, 2H), 2.25 (m, 2H), 2.47 (m, 2H), 2.70 (m, 1H), 2.85 (m, 3H), 3.55 (s, 2H), 4.68 (d, 2H), 7.03 (t, 2H), 7.58 (q, 2H).

Intermediate 19

{4-[5-(4-Fluorophenyl)-4-(2,2,2-Trifluoroethoxymethyl)-Oxazol-2-yl]-Piperidin-1-yl} Acetonitrile A 5-l round bottom flask containing sodium hydride (60% dispersion, 180 g, 4.5 mole) and tetrahydrofuran (1.5 l) is cooled to 0° C. and 2,2,2-trifluoroethanol (516 mL, 7.2 mole) is added over 1 hour. A separate 12-l round bottom flask containing {4-[5-(4-fluorophenyl)-4-hydroxymethyl-oxazol-2-yl]-piperidin-1-yl} acetonitrile (300 g, 0.90 mole), tetrahydrofuran (6.0 l) and triethylamine (500 mL, 3.6 mole) is cooled to −3° C. then methanesulfonic anhydride (360 g, 2.1 mole) is added in one portion. The resulting suspension is stirred for 30 minutes then the 2,2,2-trifluoroethanol sodium salt solution in the 5-l round bottom flask is added in one portion. The resulting slurry is warmed to room temperature, stirred for 1 hour, concentrated to a semi-solid and water (4.5 l) is added. The suspension is washed with methyl t-butylether (2×3 L). The combined organic extracts are washed with water (1.5 l), saturated aqueous sodium chloride (1.5 l), dried over sodium sulfate (100 g), filtered and concentrated to 1 l. To effect crystallization, heptane (4 l) is added. The resulting slurry is cooled to 0° C., the solids are collected by filtration and dried to constant weight to give {4-[5-(4-fluorophenyl)-4-(2,2,2-trifluoroethoxymethyl)-oxazol-2-yl]-piperidin-1-yl} acetonitrile (318 g, 0.801 mole). H NMR (400 MHz, CDCl$_3$) d 1.99 (m, 2H), 2.20 (m, 2H), 2.54 (t, 2H), 2.90 (m, 3H), 3.60 (s, 2H), 4.00 (q, 2H), 4.70 (s, 2H), 7.16 (t, 2H), 7.73 (q, 2H).

Intermediate 20

Synthetic Method 1

{4-[5-(4-Fluorophenyl)-4-(2,2,2-Trifluoroethoxymethyl)-Oxazol-2-yl]-Piperidine Hydrochloride A 5-l round bottom flask containing {4-[5-(4-fluorophenyl)-4-(2,2,2-trifluoro-ethoxymethyl)-oxazol-2-yl]-piperidin-1-yl} acetonitrile (313 g, 0.788 mole), 35% aqueous hydrazine (156 mL, 1.58 mole), 36% aqueous hydrochloric acid (130 mL, 1.58 mole), water (1 l) and ethanol (2 l) is warmed to 75° C. and stirred for 3.5 hours. The reaction mixture is cooled to room temperature, the solvent volume is reduced to 1.5 l by distillation and 3 N aqueous hydrochloric acid (1.5 l) is added. The aqueous solution is washed with dichloromethane (2×3 l). The combined organic extracts are dried over sodium sulfate (1 Kg), filtered and concentrated to effect crystallization (1.5 l). To complete the crystallization, methyl t-butylether (4 l) is added and the resulting slurry is cooled to 0° C. The solids are collected by filtration, washed with methyl t-butylether (750 mL) and dried to constant weight to give {4-[5-(4-fluorophenyl)-4-(2,2,2-trifluoro-ethoxymethyl)-oxazol-2-yl]-piperidine hydrochloride (280 g, 0.710 mole). $^1$H NMR (400 MHz, d6 DMSO) d 1.96 (m, 2H), 2.20 (m, 2H), 3.02 (q, 2H), 3.30 (m, 3H), 4.18 (q, 2H), 4.66 (s, 2H), 7.37 (t, 2H), 7.68 (q, 2H), 9.0 (bs, 1H), 9.20 (bs, 1H).

Intermediate 20

Synthetic Method 2

{4-[5-(4-Fluorophenyl)-4-(2,2,2-Trifluoroethoxymethyl)-Oxazol-2-yl]-Piperidine Hydrochloride To a 3-l round bottom flask containing thionyl chloride (21.1 mL, 291 mmole) and dichloromethane (900 mL) is added dimethyl formamide (28 mL, 364 mmole). The solution is stirred for 10 minutes then {4-[5-(4-fluorophenyl)-4-hydroxymethyl-oxazol-2-yl]-piperidin-1-yl} acetonitrile (45.9 g, 145 mmole) is added in one portion. The resulting slurry is stirred for 30 minutes then 2 N aqueous sodium hydroxide (900 mL) is added. The organic layer is separated, washed with saturated aqueous sodium chloride (500 mL), dried over sodium sulfate (100 g), filtered and concentrated to an oil. The oil is dissolved in tetrahydrofuran (120 mL) then a 0° C. solution of 1 N potassium t-butoxide in t-butanol (437 mL, 437 mmole) and 2,2,2-trifluoroethanol (40.2 mL, 582 mmole) is added. The reaction mixture is warmed to room temperature and stirred for 18 hours. The solvent volume is reduced to 100 mL by distillation, then water (700 mL) is added. The aqueous suspension is washed with methyl t-butylether (700 mL). The organic extract is washed with saturated aqueous sodium chloride then concentrated to an oil (50 mL). To the oil is added ethanol (450 mL), water (150 ml), 36% aqueous hydrochloric acid (24.3 mL, 291 mmole) and 35% aqueous hydrazine (26.6 mL, 291 mmole). The resulting solution is warmed to 80° C., stirred for 3 hours, cooled to room temperature and sodium hydroxide (17.4 g, 435 mmole) is added. The solvent volume is reduced to 320 mL by distillation and water (600 mL) is added. The aqueous suspension is washed with dichloromethane (2×500 mL). The dichloromethane extracts are washed with water, then 500 mL of a 3:2:1:1 solution of saturated aqueous sodium chloride:water:36% aqueous hydrochloric acid:ethanol. The aqueous sodium chloride:water:36% aqueous hydrochloric acid:ethanol solution is washed again with dichloromethane (500 mL). The combineed dichloromethane extracts are dried over sodium sulfate (100 g), filtered and concentrated to 250 mL to effect crystallization. To complete the crystallization, methyl t-butylether (500 mL) is added and the resulting slurry is cooled to 0° C. The solids are collected by filtration, washed with methyl t-butylether (100 mL) and dried to constant weight to give {4-[5-(4-fluorophenyl)-4-(2,2,2-trifluoroethoxymethyl)-oxazol-2-yl]-piperidine hydrochloride (47.3 g, 120 mmole). $^1$H NMR (400 MHz, d6 DMSO) d 1.96 (m, 2H), 2.20 (m, 2H), 3.02 (q, 2H), 3.30 (m, 3H), 4.18 (q, 2H), 4.66 (s, 2H), 7.37 (t, 2H), 7.68 (q, 2H), 9.0 (bs, 1H), 9.20 (bs, 1H).

Intermediate 21

N-Cyanomethyl Isonipecotic Acid

In a 12 l round bottomed flask combine isonipecotic acid (1226 g, 9.49 moles), 37% formaldehyde (850 ml) and absolute ethanol (5.0 l) and stir for thirty minutes. Sodium cyanide (470 g, 9.49 moles) is added and the reaction stirred at ambient temperature overnight. Absolute ethanol (1.3 l) and 12 M hydrochloric acid (795 ml) is added and the suspension stirred for four hours. The product is collected by vacuum filtration, washed thrice with methyl-t-butylether (3.0 l) and dried at 25 in Hg overnight to give N-cyanomethyl isonipecotic acid (1909 g, 8.05 moles) as a 1:1 mixture with sodium chloride. $^1$H NMR (400 MHz, d6 DMSO) d 1.55 (m, 2H), 1.82 (m, 2H), 2.18 (m, 3H), 2.72 (m, 2H), 3.71 (s, 2H), 12.30 (bs, 1H).

Intermediate 22

2-Chloro-1-(4'-Methoxy-3'-Sulfonamidophenyl)-Ethane

In a 500 ml round bottomed flask combine 4-(2'-chloroethyl)-anisole (17.06 g, 0.100 moles) and methylene chloride (300 ml) under $N_{2(g)}$ and chill to 0° C. Chlorosulfonic acid (57.85 g, 0.500 moles) is added dropwise, keeping the temperature below 10° C. After addition, the solution is stirred for four hours while warming to room temperature. The reaction is poured onto an ice (900 ml) 30% aqueous ammonia (200 ml) slurry and stirred for thirty minutes. The methylene chloride is removed by distillation, the slurry cooled to room temperature and the product collected by vacuum filtration. The crystals are dried at 25 in Hg overnight to give 2-chloro-1-(4'-methoxy-3'-sulfonamidophenyl)-ethane (22.94 g, 0.092 moles). $^1$H NMR (400 MHz, d6 DMSO) d 3.03 (t, 2H), 3.82 (t, 2H), 3.88 (s, 3H), 7.05 (s, 2H), 7.17 (d, 1H), 7.48 (d, 1H), 7.64 (s, 1H).

Intermediate 23

5-(2-Chloroethyl)-2-Hydroxy-Benzenesulfonamide

To a suspension of 5-(2-chloroethyl)-2-hydroxy-benzenesulfonamide (1.5 g; 6.0 mmol) in 10 ml of dichloromethane at −78°C., under nitrogen, is added a solution of boron tribromide in dichloromethane (18 ml; 1 M). The solution is brought to room temperature and stirred for five hours. The reaction mixture is poured very slowly onto ice and then partitioned between water (50 ml) and ethyl acetate (100 ml). The aqueous phase is washed once with ethyl acetate. The combined organic phases are washed with a saturated solution of sodium chloride (20 ml), dried over sodium sulfate and concentrated to dryness to afford the product as a white solid in quantitative yield (1.41 g), which is used without further purification. HNMR (CD3OD): 7.68 (d, 1H, J=2.3 Hz), 7.36 (dd, 1H, J=8.4; 2.3 Hz), 6.97 (d, 1H, J=8.4 Hz), 3.75 (t, 2H, J=7.1 Hz), 3.04 (t, 2H, J=7.1 Hz). CNMR (CD3OD): 153.3; 134.3; 129.4; 128.2; 127.6; 116.7; 44.6; 37.5.

Intermediate 24

[5-(4-Fluoro-Phenyl)-2-Piperidin-4-yl-Oxazol-4-yl] Methanol

A solution of 1-{4-[5-(4-fluoro-phenyl)-4-hydroxymethyl-oxazol-2-yl]-piperidin-1-yl}-ethanone (1.0 g; 3.14 mmol) in 95% ethanol (10 ml) is treated with a solution of sodium hydroxide (2.5 g; 62.9 mmol) in water (5 ml) and the heterogeneous mixture heated at 75 C. for three hours. The ethanol is removed in a rotary evaporator and the residue is diluted with water (10 ml) and extracted with ethyl acetate (3×20 ml) and chloroform (3×20 ml). The organic phases are washed with saturated brine (10 ml), dried over sodium sulfate and concentrated to dryness. Purification by radial chromatography on silica gel using a methanol/dichloromethane gradient (5%–30%) containing 5% triethylamine afforded the product as an orange solid (0.63 g; 73%). HNMR (CD3OD): 7.34 (dd, 2H, J=8.7; 5.6 Hz), 6.80 (t, 2H, J=8.7 Hz), 4.29 (s, 2H), 2.82 (m, 2H), 2.66 (m, 1H), 2.41 (m, 2H), 1.76 (m, 2H), 1.49 (m, 2H).

Mass spectrum: m/e calculated (MH+)=277; observed (MH+)=277.

Intermediate 25

1-{4-[5-(4-Fluoro-phenyl)-4-Methoxymethyl-Oxazol-2-yl]-Piperidin-1-yl}-Ethanone

A solution of 1-{4-[5-(4-fluoro-phenyl)-4-hydroxymethyl-oxazol-2-yl]-piperidin-1-yl}-ethanone (1.0 g; 3.14 mmol) in dry tetrahydrofuran (12 ml) is treated with sodium hydride (0.16 g; 4.09 mmol) in small portions. After 5 minutes, it is added methyl iodide (0.31 ml; 5.02 mmol) and the mixture is stirred for 45 minutes. The reaction is partitioned between ethyl acetate (40 ml) and water (15 ml). The aqueous phase is washed with ethyl acetate (15 ml). The combined organic phases are washed with saturated brine (10 ml), dried over sodium sulfate and concentrated to dryness. Purification by radial chromatography on silica gel using a methanol/ethyl acetate gradient (5%–20%) afforded the product as a light yellow oil (0.79 g; 75%). HNMR (CDCl3): 7.53 (m, 2H), 7.04 (t, 2H, J=8.7 Hz), 4.43 (m, 1H), 4.37 (s, 2H), 3.80 (m, 1H), 3.37 (s, 3H), 3.15 (m, 1H), 3.0 (ttt, 1H, J=10.8; 4.1 Hz), 2.79 (m, 1H), 2.04 (m, 2H), 2.02 (s, 3H), 1.77 (m, 2H). Mass spectrum: m/e calculated (MNa+)=355; observed (MNA+)=355.

Intermediate 26

4-[5-(4-Fluoro-Phenyl)-4-Methoxymethyl-Oxazol-2-yl]-Piperidine

A solution of 1-{4-[5-(4-fluoro-phenyl)-4-methoxymethyl-oxazol-2-yl]-piperidin-1-yl}-ethanone (0.79 g; 2.38 mmol) in ethanol (8 ml) is treated with a solution of sodium hydroxide (1.9 g; 47.59 mmol) in water (4 ml) and heated to 75 C. for 16 hours. Ethanol is removed in a rotary evaporator and the residue partitioned between ethyl acetate (100 ml) and water (20 ml). The aqueous phase is washed with ethyl acetate (2×30 ml) and chloroform (2×30 ml). The organic phases are washed with saturated brine (10 ml), dried over sodium sulfate and concentrated to dryness to afford the product as a yellow oil (0.55 g; 80%) which was used without further purification. HNMR (CDCl3): 7.53 (m, 2H), 7.02 (t, 2H, J=8.6 Hz), 4.36 (s, 2H), 3.36 (s, 3H), 3.06 (m, 2H), 2.85 (ttt, 1H, J=11.3; 3.9 Hz), 2.63 (m, 2H), 1.98 (m, 2H), 1.71 (m, 2H).

Intermediate 27

5-(4-Fluorophenyl)-2-Methylsulfanyl-Oxazole-4-Carboxylic Acid Methyl Ester

A suspension of potassium tert-butoxide (1.18 g; 10.52 mmol) in dry tetrahydrofuran (20 ml), cooled at −78 C., under argon, is treated with a solution of N-[bis(methylthio) methylene] glycine methyl ester (1.02 g; 5.26 mmol) in dry tetrahydrofuran (7 ml). After stirring for 45 minutes, it is added a solution of 4-fluorobenzoyl chloride (0.75 g; 6.31 mmol) in tetrahydrofuran (7 ml). After stirring at −78 C. for 20 minutes, it is brought to room temperature and stirred an additional 16 hours. The reaction mixture is diluted with water (30 ml) and extracted with ethyl acetate (70 ml). The aqueous phase is washed with ethyl acetate (20 ml). The combined organic phases are washed with saturated brine (20 ml), dried over sodium sulfate and concentrated to dryness. Purification by radial chromatography on silica gel using an ethyl acetate/hexane gradient (10%–70%) affords the product as a white solid (0.23 g; 16%). HNMR (CDCl3): 8.07 (m, 2H), 7.16 (t, 2H, J=8.9 Hz), 3.93 (s, 3H), 2.73 (s, 3H). Mass spectrum: m/e calculated (MH+)=268.3; observed (MH+)=268.1.

Intermediate 28

[5-(4-Fluoro-Phenyl)-2-Methylsulfanyl-Oxazol-4-]-Methanol

A solution of 5-(4-fluorophenyl)-2-methylsulfanyl-oxazole-4-carboxylic acid methyl ester (0.080 g; 0.30 mmmol) in dry dichloromethane (1.5 ml), cooled at −78 C., under argon, is treated with a solution of diisobutylaluminum hydride in hexane (1 M; 0.66 ml; 0.66 mmol) and allowed to warm to room temperature. After stirring for 15 hours, the reaction is diluted with ethyl acetate (30 ml) and 0.5 N HCl (20 ml). The aqueous phase is extracted with ethyl acetate (30 ml). The combined organic phases are washed with saturated brine (10 ml), dried over sodium sulfate and concentrated to dryness. Purification by radial chromatography on silica gel using an ethyl acetate/hexane gradient (20%–70%) affords the product as a light yellow solid (0.040 g; 56%). HNMR (CDCl3): 7.62 (m, 2H), 7.17 (t, 2H, J=8.7 Hz), 4.74 (s, 2H), 3.40 (broad s, 1H), 2.70 (s, 3H).
Mass spectrum: m/e calculated (MH+)=240.3; observed (MH+)=240.0.

Intermediate 29

5-(4-Fluoro-Phenyl)-2-Methylsulfanyl-4-(2,2,2-Trifluoro-Ethoxymethyl)-Oxazole

A suspension of [5-(4-fluoro-phenyl)-2-methylsulfanyl-oxazol-4-yl]-methanol (4.15 g; 17.34 mmol) in dry toluene (100 ml) was treated with 2,2,2-trifluoroethanol (12.63 ml; 173.4 mmol), 1,1'-(azodicarbonyl)dipiperidine (5.03 g; 19.94 mmol) and tributylphosphine (4.97 ml; 19.94 mmol) and stirred for 2 hours. The reaction mixture is partitioned between ethyl acetate (150 ml) and dilute sodium chloride solution (150 ml). The organic phase is washed with saturated brine (30 ml), dried over sodium sulfate and concentrated to dryness. Purification by flash chromatography on silica gel using an ethyl acetate/hexane gradient (2%–30%) afforded the product as a colorless residue (3.0 g; 49%). HNMR (CDCl3): 7.65 (m, 2H), 7.18 (t, 2H, J=8.7 Hz), 4.72 (s, 2H), 4.01 (qt, 2H, J=8.6 Hz), 2.73 (s, 3H). Mass spectrum: m/e calculated (MH+)=322; observed (MH+)=322.

Intermediate 30

5-(4-Fluoro-Phenyl)-2-Methanesulfonyl-4-(2,2,2-Trifluoro-Ethoxymethyl)-Oxazole

A solution of 5-(4-Fluoro-phenyl)-2-methylsulfanyl-4-(2,2,2-trifluoro-ethoxymethyl)-oxazole (3.0 g; 9.34 mmol) in dichloromethane (100 ml) is treated with 3-chloroperoxybenzoic acid (6.45 g; 37.38 mmol) and stirred for 16 hours. The reaction mixture is concentrated to dryness and partitioned between ethyl acetate (300 ml) and saturated potassium carbonate (150 ml). The organic phase is extracted with saturated potassium carbonate (3×150 ml), saturated brine (100 ml), dried over sodium sulfate and concentrated to dryness. Purification by flash chromatography on silica gel using an ethyl acetate/hexane gradient (10%–70%) affords the product as a white solid (2.70 g; 80%). HNMR (CDCl3): 7.79 (m, 2H), 7.23 (t, 2H, J=8.6 Hz), 4.79 (s, 2H), 4.03 (qt, 2H, J=8.7 Hz), 3.41 (s, 3H). Mass spectrum: m/e calculated (MH+)=354; observed (MH+)=354.

Intermediate 31

1-[5-(4-Fluoro-Phenyl)-4-(2,2,2-Trifluoro-Ethoxymethyl)-Oxazol-2-yl]-Piperazine

A solution of 5-(4-Fluoro-phenyl)-2-methanesulfonyl-4-(2,2,2-trifluoro-ethoxymethyl)-oxazole (0.30 g; 0.85 mmol) in dry dioxane (6 ml) is treated with piperazine (0.37 g; 4.25 mmol) and heated in a pressure tube at 170 C. for 16 hours. The reaction mixture is partitioned between ethyl acetate (50 ml) and water (20 ml). The aqueous phase is washed with ethyl acetate (20 ml). The combined organic phases are washed with saturated brine (10 ml), dried over sodium sulfate and concentrated to dryness. Purification by radial chromatography on silica gel using a methanol-ethyl acetate gradient (5%–20%) afforded the product as a light yellow solid (0.26 g; 86%). HNMR (CDCl3): 7.55 (m, 2H), 7.14 (t, 2H, J=8.8 Hz), 4.65 (s, 2H), 4.03 (qt, 2H, J=9.0 Hz), 3.57 (t, 4H, J=4.9 Hz), 3.01 (t, 4H, J=4.9 Hz). Mass spectrum: m/e calculated (MH+)=360; observed (MH+)=360.

EXAMPLE 1

2-Methoxy-5-{2-[4-(5-Phenyl-Oxazol-2-yl)-Piperidin-1-yl]-Ethyl}-Benzenesulfonamide A suspension of 4-(5-phenyl-oxazol-2-yl)-piperidine (253 mg, 0.96 mmol), prepared as in Intermediate 2, 5-(2-chloro-ethyl)-2-methoxy-benzenesulfonamide (335 mg, 1.34 mmol), prepared as in Intermediate 1, $K_2CO_3$ (531 mg, 3.84 mmol) and NaI (30 mg) in $CH_3CN$ (20 mL) is heated at reflux for 18 h. The solids are removed by filtration, and the solvent is evaporated. The residue is purified by chromatography on silica using 3% MeOH: $CH_2Cl_2$ as eluent to afford the product as a clear oil (193 mg). A solution of the product (193 mg, 0.44 mmol) in hot EtOH is treated with a solution of maleic acid (51 mg, 0.44 mmol) in hot EtOH. Cooling followed by filtration affords the title compound as a maleic acid salt.
$^1$H NMR (DMSO-$d_6$) d 7.68 (m, 3H), 7.62 (s, 1H), 7.47 (m, 3H), 7.36 (m, 1H), 7.19 (d, 1H, J=8.3 Hz), 7.06 (br s, 2H), 6.06 (s, 2H), 3.88 (s, 3H), 3.69 (2H, m), 3.30 (m, 5H), 3.00 (m, 2H), 2.31 (m, 2H).

EXAMPLE 2

5-{2-[4-(4-Isobutoxymethyl-5-Phenyl-Oxazol-2-yl)-Piperidin-1-yl]-Ethyl}-2-Methoxy-Benzenesulfonamide 1-[4-(4-Isobutoxymethyl-5-phenyl-oxazol-2-yl)-piperidin-1-yl]-ethanone (1.39 g, 3.9 mmol), prepared as in Intermediate 3, in MeOH (30 mL) is treated with a solution of NaOH (3.1 g, 78 mmol) in H$_2$O (10 mL) and heated at 75° C. for 18 h. The solvent is evaporated and the residue partitioned between EtOAc (200 mL) and H$_2$O (100 mL). The organic layer is dried (NA$_2$SO$_4$) and concentrated to give a light brown oil (1.1 g). A solution of the oil (750 mg, 2.5 mmol), 5-(2-chloro-ethyl)-2-methoxy-benzenesulfonamide (816 mg, 3.75 mmol), prepared as in Intermediate 1, LiBr (326 mg, 3.75 mmol), and diisopropylethylamine (0.9 mL, 5 mmol), in dioxane (40 mL) is heated at 100° C. for 18 h. The solvent is evaporated and the residue purified by chromatography on silica using 3% MeOH:CHCl$_3$ as eluent to afford the title compound as a white solid.

$^1$H NMR (CDCl$_3$) d 7.75 (d, 1H, J=2.1 Hz), 7.67 (d, 2H, J=7.4 Hz), 7.44-7.30 (m, 4H), 6.96 (d, 1H, J=8.4 Hz), 5.06 (s, 2H), 4.51 (s, 2H), 3.98 (s, 3H), 3.33 (s, J=6.7 Hz), 3.00 (m, 2H), 2.80 (m, 3H), 3.57 (m, 2H), 2.12 (m, 4H), 1.94 (m, 3H), 0.92 (d, 6H, J=6.7 Hz)

C$_{28}$H$_{37}$N$_3$O$_5$S requires C:63.73, H: 7.07, N: 7.96, found C: 63.84, H: 7.04, N: 8.02 FAB M/S m/z found 528.3 (MH$^+$)

EXAMPLE 3

5-{2-[4-(4-Ethoxymethyl-5-phenyl-oxazol-3-yl)-piperidin-1-yl]-ethyl}-2-methoxy-benzenesulfonamide To 4-(4-ethoxymethyl-5-phenyl-oxazol-2-yl)-piperidine (0.150 g), prepared as in Intermediate 4, in dioxane is added 5-(2-chloro-ethyl)-2-methoxy-benzenesulfonamide (0.170 g), prepared as in Intermediate 1, NaI (0.012 g) and DIEA (0.274 ml). After heating at 100° C. for 18 hours, the reaction mixture is partitioned between EtOAc and dilute NaHCO3 solution. The organic phase is washed with saturated brine, dried (NaSO4) and concentrated. The residue is dissolved in 1:1 MeOH-CH2Cl2 and preadsorbed onto silica gel. Purification by flash chromatography on silica gel using a MeOH-EtOAc gradient (2–20%), affords the title compound as a white solid.

$^1$H NMR (CDCl3): d 7.76 (d, 1H, J=2.1 Hz), 7.65 (d, 2H, J=7.4 Hz), 7.44 (t, 2H, J=7.4 Hz), 7.37 (m, 2H), 6.97 (d, 1H, J=8.6 Hz), 5.07 (broad s, 2H), 4.53 (s, 2H), 3.99 (s, 3H), 3.65 (q, 2H, J=7.1 Hz), 3.01 (m, 2H), 2.82 (m, 3H), 2.58 (m, 2H), 2.13 (m, 4H), 1.96 (m, 2H), 1.27 (t, 3H, J=7.1 Hz).

Mass spectrum: m/e calculated (MH+)=500.6, observed (MH+)=500.0.

EXAMPLE 4

2-Methoxy-5-(2-{4-[5-phenyl-4-(2,2,2-trifluoro-ethoxymethyl)-oxazol-2-yl]-piperidin-1-yl}-ethyl)-benzenesulfonamide To 4-[5-phenyl-4-(2,2,2-trifluoro-ethoxymethyl)-oxazol-2-yl]-piperidine (0.750 g), prepared as in Intermediate 5, in dioxane is added 5-(2-chloro-ethyl)-2-methoxy-benzenesulfonamide (0.716 g), prepared as in Intermediate 1, NaI (0.429 g) and DIEA (1.15 ml). After heating at 100° C. for 18 hours, the reaction mixture is partitioned between EtOAc and dilute NaHCO3 solution. The organic phase is washed with saturated brine, dried (NaSO4) and concentrated. The residue is dissolved in CHCl$_3$ (20 mL) and preadsorbed onto silica gel. Purification by flash chromatography on silica gel using a MeOH-EtOAc gradient (2–10%), followed by radial chromatography using a MeOH-CH$_2$Cl$_2$ gradient (1–5%) and crystallization from CH$_2$Cl$_2$-EtOAc affords the title compound as a white solid.

$^1$H NMR (CDCl3): d 7.77 (d, 1H, J=2.2 Hz), 7.67 (d, 2H, J=7.3 Hz), 7.48 (t, 2H, J=7.6 Hz), 7.40 (m, 2H), 6.99 (d, 1H, J=8.8 Hz), 5.48 (broad s, 2H), 4.73 (s, 2H), 4.01 (s, 3H), 4.00 (q, 2H, J=8.6), 3.02 (m, 2H), 2.83 (m, 3H), 2.59 (m, 2H), 2.16 (m, 4H), 1.96 (m, 2H).

Mass spectrum: m/e calculated (MH+)=554.6, observed (MH+)=554.3.

EXAMPLE 5

2-(5-{2-[4-(4-Ethoxymethyl-5-phenyl-oxazol-2-yl)-piperidin-1-yl]-ethyl}-2-methoxy-benzenesulfonylamino)-acetamide 4-(4-ethoxymethyl-5-phenyl-oxazol-2-yl)-piperidine (450 mg, 1.4 mmol), prepared as in Intermediate 4, and 2-[5-(2-chloro-ethyl)-2-methoxy-benzenesulfonylamino]-acetamide (644 mg), prepared as in Intermediate 6, LiBr (182 mg), and diisopropyl ethylamine (0.73 mL) in dioxane (15 mL) is stirred at 100° C. for 18 h. The solvent is evaporated and the residue purified by chromatography on silica using 3% MeOH:CHCl$_3$ as eluent to afford the product as a white foam.

$^1$H NMR (CDCl$_3$) d 7.68 (d, 1H, J=1.5 Hz), 7.61 (d, 2H, J=7.5 Hz), 7.42 (t, 2H, J=7.3 Hz), 7.35 (m, 2H), 6.95 (m, 2H), 5.85 (br s, 1H), 5.64 ( br s, 1H), 4.49 (s, 2H), 3.95 (s, 3H), 3.61 (q, 2H, J=7.0 Hz), 3.56 (s, 2H), 2.97 (d, 2H, J=11.4 Hz), 2.82 (m, 1H), 2.77 (t, 2H, J=7.1 Hz), 2.56 (t, 2H, J=7.6 Hz), 2.14 (t, 2H, J=11.2 Hz), 2.05 (m, 2H), 1.89 (m, 2H), 1.25 (t, 3H, J=6.8 Hz).

C$_{28}$H$_{36}$N$_4$O$_6$S-0.5 H$_2$O requires C: 59.45, H: 6.59, N: 9.90, found C: 59.12, H: 6.57, N: 9.80.

FAB MS m/z found 557.2 (MH$^+$)

EXAMPLE 6

4-(4-ethoxymethyl-5-phenyl-oxazol-2-yl)-1-[2-(4-methoxy-phenyl)-ethyl]-piperidine 1-(2-chloroethyl)-4-methoxybenzene (486 mg, 2.8 mmol), 4-(4-ethoxymethyl-5-phenyl-oxazol-2-yl)-piperidine hydrochloride (1 g, 2.2 mmol), prepared as in Intermediate 4, K$_2$CO$_3$ (393 mg, 2.85 mmol) and NaI (427 mg, 2.85 mmol) in ethanol are mixed together in a sealed tube and heated to 150° C. overnight. The mixture is cooled, filtered and concentrated. The crude material is purified by column chromatography (SiO$_2$, 10% methanol: methylene chloride), followed by another column (SiO$_2$, 15% methanol: ethyl acetate) to afford an oil which is triturated from 70% hexane; ether, 800 mg of the title compound is obtained.

NMR $^1$H (300 MHz, DMSO) d 7.6 (d, 7.7 Hz, 2H), 7.49 (t, 7.5 Hz, 2H), 7.39 (m, 1H), 7.12 (d, 7.9 Hz, 2H), 6.82 (d, 8 Hz, 2H), 4.42 (s, 2H), 3.68 (s, 3H), 3.54 (q, 2H), 3.0-2.6 (m, 7H), 2.2-1.98 (m, 4H), 1.8 (m, 2H), 1.13 (t, 6.8 Hz, 3H).

Mass Spec; [MH$^+$]=420.

C,H,N calcd for C$_{26}$H$_{31}$O$_3$N$_2$-1.5 H$_2$O. C: 69.96, H: 7.67, N: 6.27.

Found C: 70.00, H: 7.23, N: 6.24.

EXAMPLE 7

2-[2-methoxy-5-(2-{4-[5-phenyl-4-(2,2,2-triflouro-ethoxymethyl)-oxazol-2-yl]-piperidin-1-yl}-ethylbenzenesulfonylamino]-acetamide 4-(4-ethoxymethyl-5-phenyl-oxazol-2-yl)-piperidine hydrochloride (500 mg, 1.47 mmol), prepared as in Intermediate 4, 2-[5-(2-chloro-ethyl)-2-methoxy-benzenesulfonylamino]-acetamide (630 mg, 2.05 mmol), NaI (307 mg, 2.05 mmol) and diisopropyl ethylamine (0.726 ml, 4.4 mmol) are slurried in dioxane (12 ml) and heated to reflux for 72 h. The mixture is cooled, filtered, diluted with ethyl acetate, washed with water and the organic layer is dried ($Na_2SO_4$). The crude material is purified by column chromatography ($SiO_2$, 10% methanol: methylene chloride) followed by another column ($SiO_2$, 15% methanol: ethyl acetate) to afford 600 mg of the title compound as a yellow powder.

NMR $^1$H (300 MHz, DMSO) d 7.68 (d, 7.4 Hz, 2H), 7.61 (d, 2 Hz, 1H), 7.56-7.44 (m, 4H), 7.23-7.14 (m, 4H), 4.71 (s, 2H), 4.27 (q, 9.3 Hz, 2H), 3.88 (s, 3H), 3.43 (d, 5.9 Hz, 2H), 2.99-2.75 (m, 6H), 2.22-2.07 (m, 5H), 1.8-1.76 (m, 2H).

NMR $^{13}$C (75 MHz, DMSO) d 169.71, 164.99, 154.47, 147.80, 134.62, 132.22, 130.94, 129.07, 128.73, 127.43, 127.00, 125.65, 112.71, 66.46, 66.14, 65.52, 59.71, 56.13, 52.27, 45.08, 34.70, 34.24, 31.47, 29.36.

Mass Spec; [$MH^+$=611.2.

C,H,N calcd for $C_{28}H_{33}O_6N_4S_1F_3$. C: 53.50, H: 5.61, N: 8.91.

Found C: 53.50, H: 5.44, N: 9.04.

EXAMPLE 8

1-[2-(3-Carboxamidomethylaminosulfonyl-4-methoxyphenyl)-1-ethyl]-4-[4-phenyl-3-(2-methyl-1-propyloxymethyl)oxazol-2-yl]piperidine A solution of 2-[5-(2-Chloro-ethyl)-2-methoxy-benzenesulfonylamino]-acetamide (487 mg, 1.59 mmol), prepared as in Intermediate 6, and 4-[4-phenyl-3-(2-methyl-1-propyloxymethyl)oxazol-2-yl]piperidine (243 mg, 1.13 mmol) prepared as in Intermediate 7, in in 2 mL of dioxane and 1 mL of N,N-dimethylformamide is treated with diisopropylamine (0.82 mL) and lithium bromide (100 mg). The mixture is stirred at 100° C. for 14 h. The mixture is allowed to cool to 25° C. and is diluted with 100 mL of ethyl acetate. The mixture is washed with water, brine, is dried over magnesium sulfate, adn is concentrated in vacuo. Chromatography of the crude product on silica gel affords the title compound as a white amorphous solid.

$^1$H NMR (CDCl3) d 7.66 (d, J=8 Hz, 2Hz), 7.64 (s, 1H), 7.42 (t, J=8 Hz, 2H), 7.38 (d, J=8 Hz, 1H), 7.32 (t, J=8 Hz, 1H), 7.01 (bs, 1H), 6.95 (d, J=8 Hz, 1H), 5.72 (t, J=6 Hz, 1H), 5.44 (bs, 1H), 4.48 (s, 2H), 3.97 (s, 3H), 3.56 (d, J=6 Hz, 2H), 3.30 (d, J=7 Hz, 1H), 2.98 (bd, J=12 Hz, 2H), 2.80 (m, 3H), 2.58 (m, 2H), 2.17 (m, 2H), 2.08 (m, 2H), 1.86 (m, 3H), 0.90 (d, J=7 Hz, 6H) ppm.

Anal. Calcd. for C30H40N4O6S - 0.5 H2O: C, 60.69; H, 6.96; N, 9.44. Found: C, 60.70; H, 7.03; N, 9.40.

EXAMPLE 9

5-(2-{4-[5-(4-Chloro-phenyl)-4-(2,2,2-trifluoro-ethoxymethyl)-oxazol-2-yl]-piperidin-1-yl}-ethyl)-2-methoxy-benzenesulfonamide hydrochloride 4-[5-(4-chloro-phenyl)-4-(2,2,2-trifluoro-ethoxymethyl)-oxazol-2yl]-piperidine trifluoroacetate (1.1 g, 2.05 mmol), prepared as in Intermediate 12, is taken up in saturated sodium carbonate and extracted with ethyl acetate. The organics are dried over magnesium sulfate and concentrated under reduced pressure. The residue is taken up in 1,4-dioxane (70 ml) and stirred. To this solution is added 5-(2-chloro-ethyl)-2-methoxy-benzenesulfonamide (0.77 g, 3.07 mmol), prepared as in Intermediate 13, sodium iodide (0.61 g, 4.10 mmol), and diisopropyl ethyl amine (0.71 ml, 4.10 mmol) and the mixture is heated to 100° C. for 16 h. After cooling to room temperature, the solvent is removed under reduced pressure. The residue is purified by silica gel chromatography using a gradient of (1:9) methanol/ethyl acetate to (1:9) methanol/ethyl acetate with 1% ammonium hydroxide as eluant. ($R_f$=0.13 in (1:9) methanol/ethyl acetate, visualization by UV and iodoplatinate solution) The product is further purified by reverse phase HPLC using acetonitrile/water (15% to 80% gradient over 30 min) as eluant. The fractions collected are washed with saturated sodium carbonate and extracted with ethyl acetate. The organics are dried over magnesium sulfate and the solvent removed under reduced pressure. The residue is taken up in minimal ethyl acetate (5 ml) and 1M hydrochloric acid in ether is added dropwise until a precipitate formed. The solvent is removed under reduced pressure to yield the title compound.

$^1$NMR ($CD_3OD$) d 8.01 (m, 1H), 7.87 (m, 2H), 7.73 (m, 3H), 7.40 (d, 1H, J=8.5 Hz), 4.91 (s, 2H), 4.26 (q, 2H, J=9.0 Hz), 4.18 (s, 3H), 4.00 (m, 2H), 3.81 (m, 1H), 3.57 (m, 2H), 3.42 (m, 2H), 3.34 (m, 2H), 2.69 (m, 2H), 2.32 (m, 2H) high resolution FAB MS m/z found 588.15417 ($MH^+$), $C_{26}H_{29}ClF_3N_3O_5S$ requires 588.1547.

EXAMPLE 10

N-[4-(2-{4-[5-Fluoro-phenyl)-4-(2,2,2-trifluoro-ethoxymethyl)-oxazol-2-yl]-piperidin-1-yl}-ethyl)-benzyl]-methanesulfonamide A solution of 4-(2-{4-[5-(4-Fluoro-phenyl)-4-(2,2,2-trifluoro-ethoxymethyl)-oxazol-2-yl]-piperidin-1-yl}-ethyl)-benzyl amine (500 mg, 1.01 mmol), prepared as in Intermediate 10, in $CH_2Cl_2$ (30 mL) is treated with $Et_3N$ (0.2 mL, 1.41 mmol) and methanesulfonylchloride (0.09 mL, 1.21 mmol), and stirred at 23 C. for 5 h. The reaction mixture is diluted with $CH_2Cl_2$ (100 mL) and washed with saturated aqueous $NaHCO_3$ (1×80 mL), brine (1×80 mL), dried ($NaSO_4$), an concentrated to a yellow oil. The oil is purified by chromatography on silica using 3% MeOH: $CHCl_3$ as eluent to afford the title compound as a white foam.

$^1$H NMR (400 MHz, DMSO-d6) d 7.64 (m, 2H), 7.47 (t, 1H, J=6.2 Hz), 7.33 (m, 2H), 7.19 (m, 4H), 4.64 (s, 2H), 4.15 (q, 2H, J=9.4 Hz), 4.07 (d, 2H, J=6.3 Hz), 2.91 (m, 2H), 2.86 (m, 1H), 2.80 (s, 3H), 2.70 (m, 2H), 2.47 (m, 2H), 2.10 (m, 2H), 1.98 (m, 2H), 1.73 (m, 2H).

C27H31N3O4F4S requires C: 56.93; H, 5.49, N: 7.38, found C: 56.92, H: 5.54, N: 7.32.

EXAMPLE 11

2-Methoxy-5-(2-{4-[5-(2,4-difluoro-phenyl)-4-(2,2,2-trifluoro-ethoxymethyl)-oxazol-2-yl]-piperidin-1-yl}-ethyl)-benzenesulfonamide To a 100 ml round flask is added 4-[5-(2,4-Difluoro-phenyl)-4-(2,2,2-trifluoro-ethoxymethyl)-oxazol-2-yl]-piperidine, TFA salt (1.1 g, 2.25 mmol), prepared as in Intermediate 9, diisopropylethylame (1.5 mL), 1,4-dioxane (20 mL), and 5-(2-chloroethyl)-2-methoxy-benzenesulfonamide (1 g), prepared as in Intermediate 13. The flask is fitted with a reflux condensor and heated to reflux under nitrogen for 36 hours. The reaction is cooled and concentrated to a thick residue. The material is chromatographed using 5% methanol in chloroform to give 980 mg (48%) of the free base of the title compound. The material is dissolved in a minimal amount of chloroform followed by the addition of 30 ml of ethyl acetate followed by the addition of 4 ml of 1M hydrogen chloride in diethyl ether. An additional 100 ml of diethyl ether is added and the flask is allowed to stand for 16 hours. The resulting solid is filtered and dried to give the title compound.

$^1$HNMR (DMSO d6) d 10.79 (br, 1H), 7.65 (m, 2H), 7.46 (m, 2H), 7.26 (m, 1H), 7.17 (m, 1H), 7.04 (m, 2H), 4.57 (s, 0.5 H), 4.44 (s, 1.5 H), 4.09 (q, 2H, J=9.2 Hz), 3.86 (s, 2.4 H), 3.84 (s, 0.6 H), 3.64 (m, 1.6 H), 3.44 (m, 0.4 H), 3.22 (m, 2H), 3.06 (m, 3H), 2.48 (m, 2H), 2.26 (m, 2.4 H), 2.11 (m, 1.6 H).

EXAMPLE 12

2-Methoxy-5-(2-{4-[5-(4-fluoro-phenyl)-4-(2,2,2-trifluoro-ethoxymethyl)-oxazol-2-yl]-piperidin-1-yl}-ethyl)-benzenesulfonamide To 4-[5-fluoro-phenyl)-4Ο(2,2,2-trifluoro-ethoxymethyl)-oxazol-2-yl]-piperidine, trifluoroacetate salt (15.1 g, 31.9 mmol), prepared as in Intermediate 8, in dioxane (106 mL) is added 5-(2-chloroethyl)-2-methoxy-benzenesulfonamide (16 g, 63.8 mmol), prepared as in Intermediate 13, NaI (4.8 g, 31.9 mmol), LiBr (2.7 g, 31.9 mmol) and DIEA (17 mL, 96 mmol). After heating at 95° C. for 48 hours, the reaction mixture is allowed to cool, and diluted with EtOAc (300 mL). The organic phase is washed with H$_2$O (2×100 mL), saturated brine (1×100 mL), dried (Na$_2$SO$_4$) and concentrated. The residue is purified by chromatography on silica gel using 5% MeOH:EtOAc with 1% NH$_4$OH and the appropriate fractions are combined and concentrated to a solid. The solid is triturated with Et$_2$O to afford the title compound as a beige solid (alternatively named).

$^1$H NMR (400 MHz, DMSO-d$_6$) d 7.65 (m, 2H), 7.56 (d, 1H, J=1.8 Hz), 7.39 (dd, 1H, J=8.4, 1.8 Hz), 7.33 (t, 2H, J=8.8 Hz), 7.08 (d, 1H, J=8.3 Hz), 6.98 (s, 2H), 4.64 (s, 2H), 4.15 (dd, 2H, J=18.7, 9.3 Hz), 3.83 (s, 3H), 2.92 (m, 2H), 2.83 (m, 1H), 2.71 (bt, J=7.2 Hz), 2.44 (m, 2H), 2.10 (m, 2H), 1.98 (m, 2H), 1.74 (m, 2H) Reverse phase HPLC using acetonitrile:water (15% to 80% gradient over 30 min, 0.1% TFA) as eluant t$_r$=14.8 min, FAB MS m/z found 572.2 (MH$^+$)
Anal. Calcd. for C$_{26}$H$_{26}$N$_3$O$_5$: C, 54.6, H, 5.1; N, 7.4. Found: C, 54.2; H, 5.2; N, 7.3

EXAMPLE 13

5-(2-{4-[5-(4-fluorophenyl)-4-(2,2,2-trifluoroethoxymethyl)-oxazol-2-yl}-ethyl)-2-methoxybenzenesulfonamide hydrochloride To a 22-l round bottom flask is added 5-(2-{4-[5-(4-fluorophenyl)-4-(2,2,2-trifluoroethoxymethyl)-oxazol-2-yl}-ethyl)-2-methoxybenzenesulfonamide (695 g, 1.22 mole) and methanol (12 l). The slurry is warmed until a solution results (60° C.). The hot solution is filtered through sintered glass into a round bottom flask and the solvent volume is reduced to 3 l by distillation. To the resulting slurry is added 0.5N aqueous hydrochloric acid (7 l). The resulting slurry is stirred at room temperature for 1 hour, cooled to 5° C. and the solids are collected by filtration (mixture of form I and form II crystal forms). The still damp solids are transfered to a 22-l round bottom flask then water (14 l) is added. The resulting slurry is warmed to 70° C. and stirred for 2 hours. This transforms all of the form I crystal to form II cyrstal (monitored by DSC). When crystal form conversion is complete, the slurry is cooled to 5° C., the solids are collected by filtration, washed with water (2×200 mL) and dried to constant weight to give 5-(2-{4-[5-(4-fluorophenyl)-4-(2,2,2-trifluoroethoxymethyl)-oxazol-2-yl}-ethyl)-2-methoxybenzenesulfonamide. hydrochloride (715 g, 1.18 mole) as the form II solid. $^1$H NMR (400 MHz, d6, DMSO) d 2.05-2.48 (m, 4H), 3.0-3.75 (m, 9H), 3.9 (s, 3H), 4.20 (q, 2H), 4.71 (s, 2H), 7.07 (m, 2H), 7.20 (m, 1H), 7.37 (t, 2H), 7.48 (m, 1H), 7.70 (m, 3H), 10.95 (bs, 1H).

EXAMPLE 14

5-(20{4-[5-(4-Fluorophenyl)-4-(2,2,2-Trifluoroethoxymethyl)-Oxazol-2yl}-Ethyl)-2-Methoxybenzenesulfonamide A 12-l round bottom flask is charged with dimethylformamide (4.5 l), warmed to 80° C. then sodium iodide (360 g, 2.4 mole) and 2-chloro-1-(4'-methoxy-3'-sulfonamidophenyl)-ethane (513 g, 2.06 mole) are added. The reaction mixture is warmed to 105° C. then potassium carbonate (656 g, 4.75 mole) and {4-[5-(4-fluoro-phenyl)-4-(2,2,2-trifluoroethoxymethyl)-oxazol-2-yl]-piperidine hydrochloride (625 g, 1.58 mole) are added. The resulting slurry is stirred at 105° C. for 45 minutes then cooled to 50° C. and water (7 l) is added. The resulting slurry is cooled to room temperature, stirred for 15 hours then cooled to 5° C. The solids are collected by filtration then washed with water (2 l). The still damp solids are dissolved in warm ethanol (12 l). The hot ethanol solution is vacuum filtered through sintered glass and the filtrate volume is reduced by distillation to 7 l to effect crystallization. The slurry is cooled to 5° C., the solids are collected by filtration, washed with water (2 l) and dried to constant weight to give 5-(2-{4-[5-(4-fluorophenyl)-4-(2,2,2-trifluoroethoxymethyl)-oxazol-2-yl}-ethyl)-2-methoxybenzenesulfonamide (695 g, 1.22 mole). $^1$H NMR (400 MHz, d6, DMSO) d 1.73 (m, 2H), 2.0 (d, 2H), 2.10 (t, 2H), 2.49 (m, under dmso peak, 2H), 2.72 (m, 2H), 2.85 (m, 1H), 2.92 (m, 2H), 3.85 (s, 3H), 4.17 (q, 2H), 4.65 (s, 2H), 7.02 (s, 2H), 7.11 (d, 1H), 7.35 (t, 2H), 7.45 (dd, 1H), 7.55 (s, 1H), 7.68 (m, 2H).

EXAMPLE 15

5-(2-{4-[5-(4-Fluoro-phenyl)-4-(2,2,2-trifluoro-ethoxymethyl)-oxazol-2-yl]-piperidin-1-yl}-ethyl)-2-hydroxy-benzenesulfonamide.

To a solution of 4-[5-(4-fluoro-phenyl)-4-trifluoro-ethoxymethyl-oxazol-2-yl]-piperidine (0.25 g; 0.70 mmol) in dry dioxane (6 ml) is added 5-(2-chloroethyl)-2-hydroxy-benzenesulfonamide (0.33 g; 1.40 mmol), sodium iodide (0.21 g; 1.40 mmol) and diisopropylethylamine (0.48 ml; 2.79 mmol). The mixture is heated at 100 C. for 16 hours, cooled and partitioned between ethyl acetate (30 ml) and dilute sodium bicarbonate (10 ml). The aqueous phase is washed with ethyl acetate (2×15 ml). The combined organic phases are washed with a saturated solution of sodium chloride (10 ml), dried over sodium sulfate and concentrated to dryness. Purification by radial chromatography on silica gel using a methanol-ethyl acetate gradient (5%–20%), followed by crystallization from ethanol-ethyl acetate afforded the product as a white solid (0.19 g; 47% yield). HNMR (DMSO): 7.70 (dd, 2H, J=8.8; 5.4 Hz), 7.52 (d, 1H, J=2.2 Hz), 7.38 (t, 2H, J=8.8 Hz), 7.29 (dd, 1H, J=8.4; 2.2 Hz), 6.92 (d, 1H, J=8.4 Hz), 4.69 (s, 2H), 4.21 (q, 2H, J=9.5 Hz), 3.35 (broad s, 2H), 2.97 (m, 2H, 2.88 (m, 1H), 2.71 (m, 2H), 2.49 (m, 2H), 2.15 (m, 2H), 2.05 (m, 2H), 1.78 (m, 2H). Mass spectrum: m/e calculated (MH+)=558.6; observed (MH+)=558.5.

EXAMPLE 16

5-(2-{4-[5-(4-Fluoro-phenyl)-4-hydroxymethyl-oxazol-2-yl]-piperidin-1-yl}-ethyl)-2-methoxy-benzenesulfonamide A solution of [5-(4-fluoro-phenyl)-2-piperidin-4-yl-oxazol-4-yl-oxazol-4-yl]-methanol (0.20 g; 0.72 mmol) in dry dioxane (6 ml) is treated with 5-(2-chloroethyl)-2-methoxy-benzenesulfonamide (0.36 g; 1.45 mmol), sodium iodide (0.22 g; 1.45 mmol) and diisopropylethylamine (0.50 ml; 2.88 mmol) and heated to 100 C. for 16 hours. The reaction is cooled and partitioned between ethyl acetate (30 ml) and dilute sodium bicarbonate (10 ml). The aqueous phase is washed with ethyl acetate (2×15 ml). The combined organic phases are washed with saturated brine (10 ml), dried over sodium sulfate and concentrated to dryness. Purification by radial chromatography on silica gel, using a methanol/ethyl acetate gradient (2%–25%), followed by trituration from hot ethanol afforded the product as a white solid (0.10 g; 46%).
HNMR (DMSO: 7.76 (m, 2H), 7.64 (d, 1H, J=2.2 Hz), 7.47 (dd, 1H, J=8.4; 2.2 Hz), 7.37 (t, 2H, J=8.8 Hz), 7.16 (d, 1H, J=8.4 Hz), 7.05 (s, 2H), 5.35 (t, 1H, J=5.0 Hz), 4.48 (d, 2H, J=5.0 Hz), 3.90 (s, 3H), 3.01 (m, 3H), 2.82 (m, 4H), 2.09 (m, 4H), 1.82 (m, 2H). Mass spectrum: m/e calculated (MH+)= 490.6; observed (MH+)=489.9.

EXAMPLE 17

5-(2-{4-[5-(4-Fluoro-phenyl)-4-hydroxymethyl-oxazol-2-yl]-piperidin-1-yl}-ethyl)-2-hydroxy-benzenesulfonamide A solution of [5-(4-fluoro-phenyl)-2-piperidin-4-yl-oxazol-4-yl]methanol (0.20 g; 0.72 mmol) in dry dioxane (6 ml) is treated with 5-(2-chloroethyl)-2-hydroxy-benzenesulfonamide (0.36 g; 1.45 mmol), sodium iodide (0.22 g; 1.45 mmol) and diisopropylethylamine (0.50 ml; 2.88 mmol) and heated to 100 C. for 16 hours. The reaction is cooled and partitioned between ethyl acetate (30 ml) and water (10 ml). The aqueous phase is washed with ethyl acetate (2×15 ml), dried over sodium sulfate and concentrated to dryness. Purification by radial chromatography using a methanol/ethyl acetate gradient (5%–40%) is followed by a second chromatography using a methanol/dichloromethane gradient (5%–30%). Crystallization from methanol/ethyl acetate afforded the product as a white solid (0.055 g; 16%). HNMR (CD3OD): 7.75 (m, 2H), 7.64 (d, 1H, J=2.1 Hz), 7.31 (dd, 1H, J=8.4; 2.1 Hz), 7.23 (t, 2H, J=8.8 Hz), 6.92 (d, 1H, J=8.4 Hz), 4.63 (s, 2H), 3.12 (m, 2H), 2.96 (m, 1H), 2.82 (m, 2H), 2.66 (m, 2H), 2.34 (m, 2H), 2.17 (m, 2H), 1.99 (m, 2H). Mass spectrum: m/e calculated (MH+)=476.6; observed (MH+)=476.2.

EXAMPLE 18

5-(2-{4-[5-(4-Fluoro-phenyl)-4-methoxymethyl-oxazol-2-yl]-piperidin-1-yl}-ethyl)-2-methoxy-benzenesulfonamide A solution of 4-[5-(4-fluoro-phenyl)-4-methoxymethyl-oxazol-2-yl]-piperidine (0.3 g; 1.03 mmol) in dry dioxane (7 ml) is treated with 5-(2-chloroethyl)-2-methoxy-benzenesulfonamide (0.52 g; 2.06 mmol), sodium iodide (0.31 g; 2.06 mmol) and diisopropylethylamine (0.72 ml; 4.12 mmol) and heated to 100 C. for 16 hours. The reaction mixture is partitioned between ethyl acetate (50 ml) and dilute sodium bicarbonate (20 ml). The aqueous phase is washed with ethyl acetate (20 ml). The combined organic phases are washed with saturated brine (10 ml), dried over sodium sulfate and concentrated to dryness. Purification by radial chromatography on silica gel using a methanol/ethyl acetate gradient (5%–20%) is followed by a second chromatography using a methanol/dichloromethane gradient (5%–15%). Crystallization from dichloromethane/ethyl acetate afforded the product as a white solid (0.20 g; 40%). HNMR (CDCl3): 7.72 (d, 1H, J=2.1 Hz), 7.62 (m, 2H), 7.35 (dd, 1H, J=8.6; 2.1 Hz), 7.13 (t, 21H, J=8.6 Hz), 6.96 (d, 1H, J=8.6 Hz), 5.64 (broad s, 2H), 4.44 (s, 2H), 3.97 (s, 3H), 3.44 (s, 3H), 2.96 (m, 2H), 2.80 (m, 1H), 2.75 (m, 2H), 2.53 (m, 2H), 2.10 (m, 4H), 1.90 (m, 2H). Mass spectrum: m/e calculated (MH+)=504; observed (MH+)=504.

EXAMPLE 19

5-(2-{4-[5-(4-Fluoro-phenyl)-4-(2,2,2-trifluoro-ethoxymethyl)-oxazol-2-yl]-piperazin-1-yl}-ethyl)-2-methoxy-benzenesulfonamide A solution of 1-[5-(4-fluoro-phenyl)-4-(2,2,2-trifluoro-ethoxymethyl)-oxazol-2-yl]-piperazine (0.15 g; 0.42 mmol) in dry dioxane (5 ml) is treated with 5-(2-chloroethyl)-2-methoxy-benzenesulfonamide (0.25 g; 1.0 mmol), sodium iodide (0.15 g; 1.0 mmol) and diisopropylethylamine (0.36 ml; 2.09 mmol) and heated to 100 C. for 16 hours. The reaction mixture is partitioned between ethyl acetate (40 ml) and dilute sodium bicarbonate (20 ml). The aqueous phase is extracted with ethyl acetate (20 ml). The combined organic phases are washed with saturated brine (10 ml), dried over sodium sulfate and concentrated to dryness. Purification by radial chromatography on silica gel using a methanol-ethyl acetate gradient (1%–20%) is followed by a second chromatography using a methanol-dichloromethane gradient (1%–5%). Crystallization from ethyl acetate/hexane affords the product as a white solid (0.14 g; 56%). HNMR (CDCL3): 7.81 (d, 1H, J=2.4 Hz), 7.54 (m, 2H), 7.42 (dd, 1H, J=8.7, 2.0 Hz), 7.14 (t, 2H, J=8.8 Hz), 7.02 (d, 1H, J=8.7 Hz), 5.16 (s, 2H), 4.04 (s, 3H), 4.01 (qt, 2H, J=8.8 Hz), 3.62 (m, 4H), 2.85 (m, 2H), 2.66 (m, 6H).
Mass spectrum: m/e calculated (MH+)=573.6; observed (MH+)=573.3.

EXAMPLE 20

Core tablets containing compounds of formula I according to the present invention are formed into tablet using the following ingredients: 0.224 weight percent 5-(2-{4-[5-(4-fluorophenyl)-4-(2,2,2-trifluoroethoxymethyl)-oxazol-2yl}-ethyl)-2-methoxy benzenesulfonamide hydrochloride, 94.025 weight percent microcrystalline cellulose, 5 weight percent sodium starch glycolate NF, and 0.750 weight percent magnesium stearate. The subject ingredients are thoroughly mixed and pressed into tablets according to techniques well known to the person of ordinary skill in the art. Tablets so formed have the following unit quantities in milligrams per tablet:

| Active Agent | 1.12 |
|---|---|
| Microcrystalline Cellulose | 470.13 |
| Sodium Starch Glycolate | 25.00 |
| Magnesium Stearate | 3.75 |

Tablets so made have an effective dosage of 1 mg of 5-(2-{4-[5-(4-fluorophenyl)-4-(2,2,2-trifluoroethoxymethyl)-oxazol-2-yl}-ethyl)-2-methoxybenzenesulfonamide hydrochloride.

EXAMPLE 21

Core tablets containing compounds of formula I according to the present invention are formed into tablet using the following ingredients: 0.56 weight percent 5-(2-{4-[5-(4-fluorophenyl)-4-(2,2,2-trifluoroethoxymethyl)-oxazol-2-yl}-ethyl)-2-methoxy benzenesulfonamide hydrochloride, 93.69 weight percent microcrystalline cellulose, 5 weight percent sodium starch glycolate NF, and 0.750 weight percent magnesium stearate. The subject ingredients are thoroughly mixed and pressed into tablets according to techniques well known to the person of ordinary skill in the art. Tablets so formed have the following unit quantities in milligrams per tablet:

| Active Agent | 2.80 |
|---|---|
| Microcrystalline Cellulose | 468.45 |
| Sodium Starch Glycotate | 25.00 |
| Magnesium Stearate | 3.70 |

Tablets so formed have an effective dosage of 2.5 mg of 5-(2-{4-[5-(4-fluorophenyl)-4-(2,2,2-trifluoroethoxymethyl)-oxazol-2yl}-ethyl)-2-methoxybenzenesulfonamide hydrochloride.

EXAMPLE 22

Core tablets containing compounds of formula I according to the present invention are formed into tablet using the following ingredients: 1.12 weight percent 5-(2-{4-[5-(4-fluorophenyl)-4-(2,2,2-trifluoroethoxymethyl)oxazol-2yl}-ethyl)-2-methoxy benzenesulfonamide hydrochloride, 93.13 weight percent microcrystalline cellulose, 5 weight percent sodium starch glycolate NF, and 0.750 weight percent magnesium stearate. The subject ingredients are thoroughly mixed and pressed into tablets according to techniques well known to the person of ordinary skill in the art. Tablets so formed have the following unit quantities in milligrams per tablet:

| Active Agent | 5.60 |
|---|---|
| Microcrystalline Cellulose | 465.65 |
| Sodium Starch Glycolate | 25.00 |
| Magnesium Stearate | 3.75 |

Tablets so formed have an effective dosage of 5 mg of 5-(2-{4-[5-(4-fluorophenyl)-4-(2,2,2-trifluoroethoxymethyl)-oxazol-2-yl}-ethyl)-2-methoxybenzenesulfonamide hydrochloride.

EXAMPLE 23

Core tablets containing compounds of formula I according to the present invention are formed into tablet using the following ingredients: 5.6 weight percent 5-(2-{4-[5-(4-fluorophenyl)-4-(2,2,2-trifluoroethoxymethyl)oxazol-2yl}-ethyl)-2-methoxy benzenesulfonamide hydrochloride as the pharmaceutically active agent, 88.45 weight percent microcrystalline cellulose, 5 weight percent sodium starch glycolate NF, 0.20 percent weight percent colloidal silica and 0.750 weight percent magnesium stearate. The subject ingredients are thoroughly mixed and pressed into tablets according to techniques well known to the person of ordinary skill in the art. Tablets so formed have the following unit quantities in milligrams per tablet:

| Active Agent | 28.00 |
|---|---|
| Microcrystalline Cellulose | 442.25 |
| Sodium Starch Glycolate | 25.00 |
| Colloidal Silica | 1.00 |
| Magnesium Stearate | 3.75 |

Tablets so formed have an effective dosage of 25 mg of 5(2-{4-[5-(4-fluorophenyl)-4-(2,2,2-trifluoroethoxymethyl)oxazol-2-yl}-ethyl)-2-methoxybenzenesulfonamide hydrochloride.

What is claimed is:

1. An oxazole compound of formula (I):

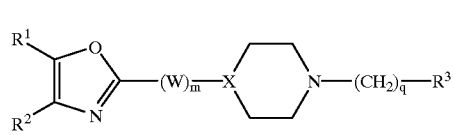

wherein:

$R^1$ and $R^3$ are selected from the group consisting of phenyl or phenyl mono- or disubstituted with $C_{1-6}$alkyl, halogen, hydroxy, $C_{1-6}$alkoxy, aminosulfonyl, $C_{1-6}$alkylsulfonylamino $C_{1-6}$alkyl or carbamyl$C_{1-6}$alkylaminosulfonyl;

$R^2$ is selected from hydrogen, $C_{1-6}$alkyl, $C_{1-6}$alkoxy, hydroxy$C_{1-6}$alkyl, $C_{1-6}$alkoxy $C_{1-6}$alkyl or (fluorinated $C_{1-6}$alkyl)oxy $C_{1-6}$alkyl;

W is a $C_{1-6}$alkylene chain;

m is the integer 0;

X is CH; and q is independently an integer selected from the group consisting of 1, 2, 3 or 4;

or a pharmaceutically acceptable salt thereof.

2. A compound as claimed in claim 1 wherein q is 2.

3. A compound as claimed in claim 1 wherein
   $R^1$ is phenyl or phenyl mono or disubstituted with halogen; and
   $R^3$ is phenyl mono or disubstituted with hydroxy, $C_{1-6}$alkoxy, aminosulfonyl, $C_{1-6}$alkylsulfonylamino$C_{1-6}$alkyl or carbamyl$C_{1-6}$alkylaminosulfonyl.

4. A compound as claimed in claim 1 wherein $R^3$ is 4-hydroxy or $C_{1-6}$alkoxyphenyl optionally substituted in the meta-position by aminosulfonyl or carbamyl$C_{1-6}$ alkylaminosulfonyl.

5. A compound as claimed in claim 7 wherein $R^3$ is 4-hydroxy or methoxyphenyl optionally substituted in the meta position by aminosulfonyl or carbamylmethylaminosulfonyl.

6. A compound as claimed in claim 1 wherein $R^2$ is hydrogen, hydroxy$C_{1-6}$alkyl, $C_{1-6}$alkoxy$C_{1-6}$alkyl, or (fluorinated $C_{1-6}$alkyl)oxy$C_{1-6}$alkyl.

7. A compound as claimed in claim 1 wherein $R^2$ is $C_{1-6}$alkoxy$C_{1-6}$alkyl or (fluorinated $C_{1-6}$alkyl)oxy$C_{1-6}$alkyl.

8. A compound as claimed in claim 1 wherein $R^2$ is ethoxymethyl or 2,2,2-trifluoroethoxymethyl.

9. A compound selected from the group consisting of:
   2-Methoxy-5-{2-[4-(5-phenyl-oxazol-2-yl)-piperidin-1-yl]-ethyl}-benzenesulfonamide;
   5-{2-[4-(4-isobutoxymethyl-5-phenyl-oxazol-2-yl)-piperidin-1-yl]-ethyl}-2-methoxy-benzenesulfonamide;
   5-{2-[4-(4-Ethoxymethyl-5-phenyl-oxazol-2-yl)-piperidin-1-yl]-ethyl)-2-methoxy-benzenesulfonamide;
   2-Methoxy-5-(2-{4-[5-phenyl-4-(2,2,2-trifluoro-ethoxymethyl)-oxazol-2-yl]-piperidin-1-yl}-ethyl)-benzenesulfonamide;
   2-(5-{2-[4-(4-Ethoxymethyl-5-phenyl-oxazol-2-yl)-piperidin-1-yl]-ethyl}-2-methoxy-benzenesulfonylamino)-acetamide;
   4-(4-ethoxymethyl-5-phenyl-oxazol-2yl)-1-[2-(4-methoxy-phenyl)-ethyl]-piperidine;
   2-[2-methoxy-5-(2-{4-[5-phenyl-4-(2,2,2-trifluoro-ethoxymethyl)-oxazol-2yl]-piperidin-1-yl}-ethylbenzenesulfonylamino]-acetamide;
   1-[2-(3-Carboxamidomethylaminosulfonyl-4-methoxyphenyl)-1-ethyl]-4-[4-phenyl-3-(2-methyl-1-propyloxymethyl)oxazol-2yl]piperidine;
   5-(2-{4-[5-(4-Chloro-phenyl)-4-(2,2,2-trifluoro-ethoxymethyl)-oxazol-2-yl]-piperidin-1-yl}-ethyl)-2-methoxy-benzenesulfonamide hydrochloride;
   N-[4-(2-{4-[5-(4-Fluoro-phenyl)-4-(2,2,2-trifluoro-ethoxymethyl)-oxazol-2-yl]-piperidin-1-yl}-ethyl)-benzyl]-methanesulfonamide;
   5-(2-{4-[5-(4-Fluoro-phenyl)-4-(2,2,2-trifluoro-ethoxymethyl)-oxazol-2-yl]-piperazin-1-yl}-ethyl)-2-methoxy-benzenesulfonamide;
   2-Methoxy-5-(2-{4-[5-(2,4-difluoro-phenyl)-4-(2,2,2-trifluoro-ethoxymethyl)-oxazol-2-yl]-piperidin-1-yl}-ethyl)-benzenesulfonamide;
   5-(2-{4-[5-(4-Fluoro-phenyl)-4-(2,2,2-trifluoro-ethoxymethyl)-oxazol-2-yl]-piperidin-1-yl}-ethyl)-2-hydroxy-benzenesulfonamide;
   5-(2-{4-[5-(4-Fluoro-phenyl)-4-hydroxymethyl-oxazol-2-yl]-piperidin-1-yl}-ethyl)-2-methoxy-benzenesulfonamide;
   5-(2-{4-[5-(4-Fluoro-phenyl)-4-hydroxymethyl-oxazol-2-yl]-piperidin-1-yl}-ethyl)-2-hydroxy-benzenesulfonamide;
   5-(2-{4-[5-(4-Fluoro-phenyl)-4-methoxymethyl-oxazol-2-yl]-piperidin-1-yl}-ethyl)-2-methoxy-benzenesulfonamide; and
   5-(2-{4-[5-(4-Fluoro-phenyl)-4-(2,2,2-trifluoro-ethoxymethyl)-oxazol-2-yl]-piperazin-1-yl}-ethyl)-2-methoxy-benzenesulfonamide.

10. An oxazole compound of formula (I):

$$R^1\text{-oxazole-}(W)_m\text{-X-N-}(CH_2)_q\text{-}R^3 \quad (I)$$

wherein:
   $R^1$ and $R^3$ are selected from the group consisting of phenyl or phenyl mono- o disubstituted with $C_{1-6}$alkyl, halogen, $C_{1-6}$alkoxy, aminosulfonyl, $C_{1-6}$alkylsulfonylamino$C_{1-6}$alkyl, or carbamyl$C_{1-6}$alkylaminosulfonyl;
   $R^2$ is selected from hydrogen, $C_{1-6}$alkyl, $C_{1-6}$alkoxy $C_{1-6}$alkyl or (fluorinated $C_{1-6}$alkyl)oxy$C_{1-6}$alkyl;
   W is a $C_{1-6}$alkylene chain;
   m is the integer 0;
   X is CH; and
   q is independently an integer selected from the group consisting of 1, 2, 3 or 4;
   or a pharmaceutically acceptable acid-addition or base-addition salt thereof.

11. A pharmaceutical composition comprising a compound of claim 1 and a pharmaceutically acceptable diluent or carrier.

12. A method for the treatment of benign prostatic hyperplasia, cardiac arrhythmia, glaucoma, male pattern baldness or a hypertension which comprises administering to a patient in need of such treatment a compound as defined in claim 1.

13. The method of claim 12 wherein said method is for the treatment of benign prostatic hyperplasia.

14. The method of claim 13 wherein said compound is administered to a patient in combination with a testosterone 5α-reductase inhibitor or a dopamine $D_2$-antagonist.

* * * * *